United States Patent
Shiono et al.

(10) Patent No.: US 10,352,853 B2
(45) Date of Patent: Jul. 16, 2019

(54) MEASURING DEVICE INCLUDING LIGHT SOURCE THAT EMITS AT LEAST ONE LIGHT PULSE GROUP, PHOTODETECTOR, AND CONTROL CIRCUIT

(71) Applicant: Panasonic Intellectual Property Management Co., Ltd., Osaka (JP)

(72) Inventors: Teruhiro Shiono, Osaka (JP); Tatsuya Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/016,624

(22) Filed: Jun. 24, 2018

(65) Prior Publication Data

US 2019/0017932 A1 Jan. 17, 2019

(30) Foreign Application Priority Data

Jul. 12, 2017 (JP) .................................. 2017-135859

(51) Int. Cl.
| | |
|---|---|
| *G01N 21/39* | (2006.01) |
| *G01N 33/49* | (2006.01) |
| *A61B 5/00* | (2006.01) |
| *G01N 21/47* | (2006.01) |
| *G01N 21/31* | (2006.01) |

(52) U.S. Cl.
CPC .......... *G01N 21/39* (2013.01); *A61B 5/0059* (2013.01); *G01N 21/474* (2013.01); *G01N 33/49* (2013.01); *G01N 21/314* (2013.01); *G01N 2021/399* (2013.01); *G01N 2201/0697* (2013.01)

(58) Field of Classification Search
CPC ...... G01N 21/39; G01N 21/474; G01N 33/49; G01N 21/314; A61B 5/0059
See application file for complete search history.

(56) References Cited

U.S. PATENT DOCUMENTS 4,012,145 A * 3/1977 Chabannes ............ G01N 21/39
356/320
5,386,819 A 2/1995 Kaneko et al.
(Continued)

FOREIGN PATENT DOCUMENTS

JP 3-279843 12/1991
JP 2002-168862 6/2002
(Continued)

*Primary Examiner* — Roy M Punnoose
(74) *Attorney, Agent, or Firm* — McDermott Will & Emery LLP

(57) ABSTRACT

A measuring device includes: a light source that emits, toward a target part of an object, at least one light pulse group each including light pulses emitted sequentially, a photodetector that detects at least a part of at least one reflected light pulse group and including reflected light pulses sequentially returning from the target part, and a control circuit that controls the light source and the photodetector. The control circuit causes the light source to emit the at least one light pulse group within a first period, causes the photodetector to extract, within the first period, a first component that is a component of light included in at least a part of a leading reflected light pulse of the reflected light pulses, and causes the photodetector to output a first electric signal corresponding to the first component.

17 Claims, 18 Drawing Sheets

(56) References Cited

U.S. PATENT DOCUMENTS

| | | | | |
|---|---|---|---|---|
| 5,812,257 | A * | 9/1998 | Teitel | G01S 7/06 |
| | | | | 342/463 |
| 6,757,068 | B2 * | 6/2004 | Foxlin | G02B 27/017 |
| | | | | 356/139.03 |
| 7,301,648 | B2 * | 11/2007 | Foxlin | G02B 27/017 |
| | | | | 356/620 |
| 7,893,840 | B2 * | 2/2011 | Volpi | G01S 13/66 |
| | | | | 340/572.1 |
| 10,198,874 | B2 * | 2/2019 | Dearman | G06F 3/011 |
| 2002/0071122 | A1 * | 6/2002 | Kulp | G01M 3/38 |
| | | | | 356/437 |
| 2009/0009595 | A1 | 1/2009 | Ishiwata et al. | |
| 2010/0056887 | A1 | 3/2010 | Kimura et al. | |
| 2011/0245642 | A1 | 10/2011 | Minetoma | |
| 2017/0196467 | A1 * | 7/2017 | Shiono | A61B 5/0261 |
| 2018/0338690 | A1 * | 11/2018 | Shiono | A61B 5/0042 |
| 2019/0014994 | A1 * | 1/2019 | Shiono | A61B 5/0261 |

FOREIGN PATENT DOCUMENTS

| | | |
|---|---|---|
| JP | 2003-337102 | 11/2003 |
| JP | 2007-260123 | 10/2007 |
| JP | 2011-196693 | 10/2011 |
| JP | 2011-217798 | 11/2011 |
| JP | 2017-011693 | 1/2017 |
| JP | 2017-053866 | 3/2017 |
| WO | 2008/065699 | 6/2008 |

* cited by examiner

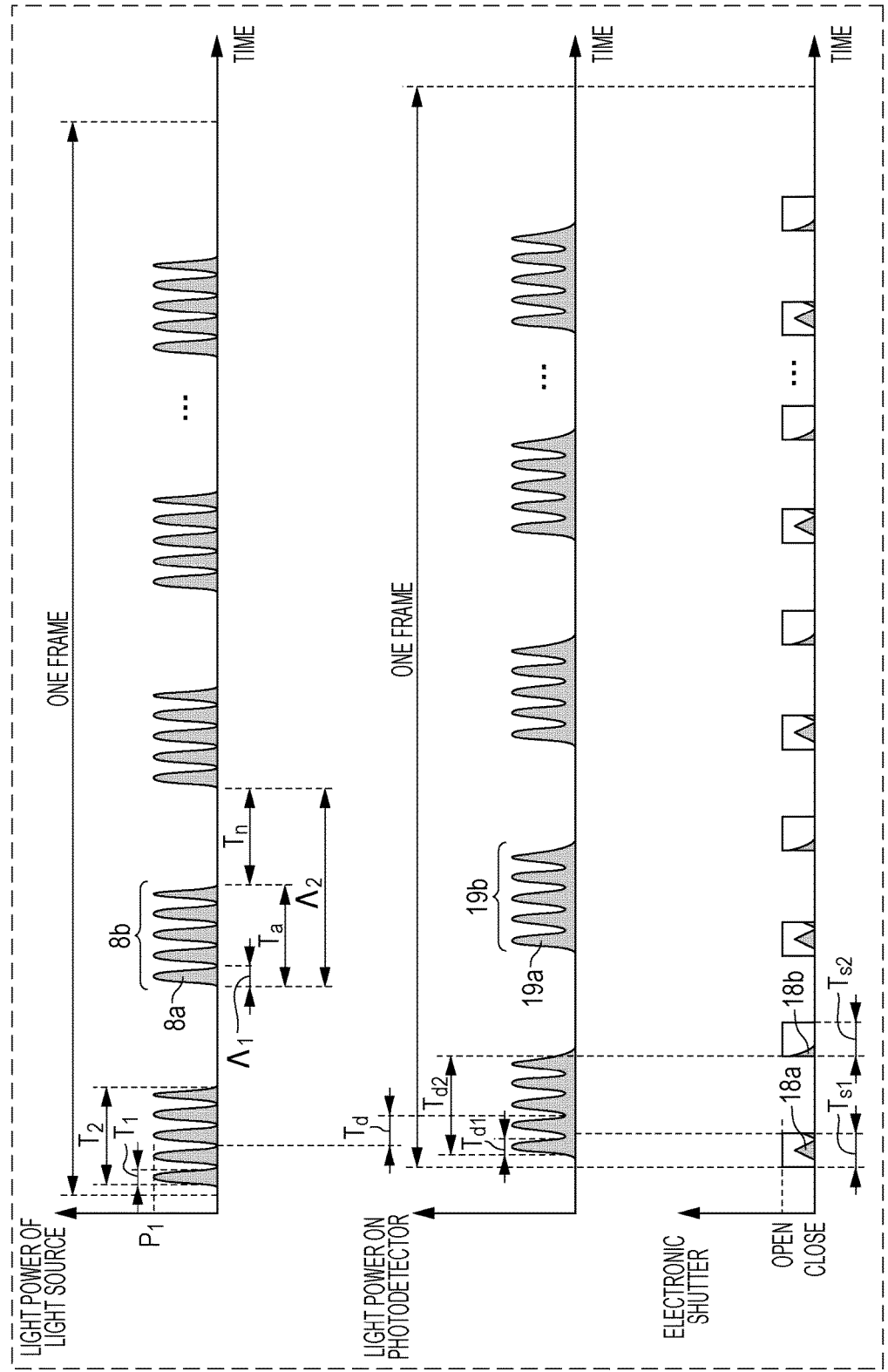

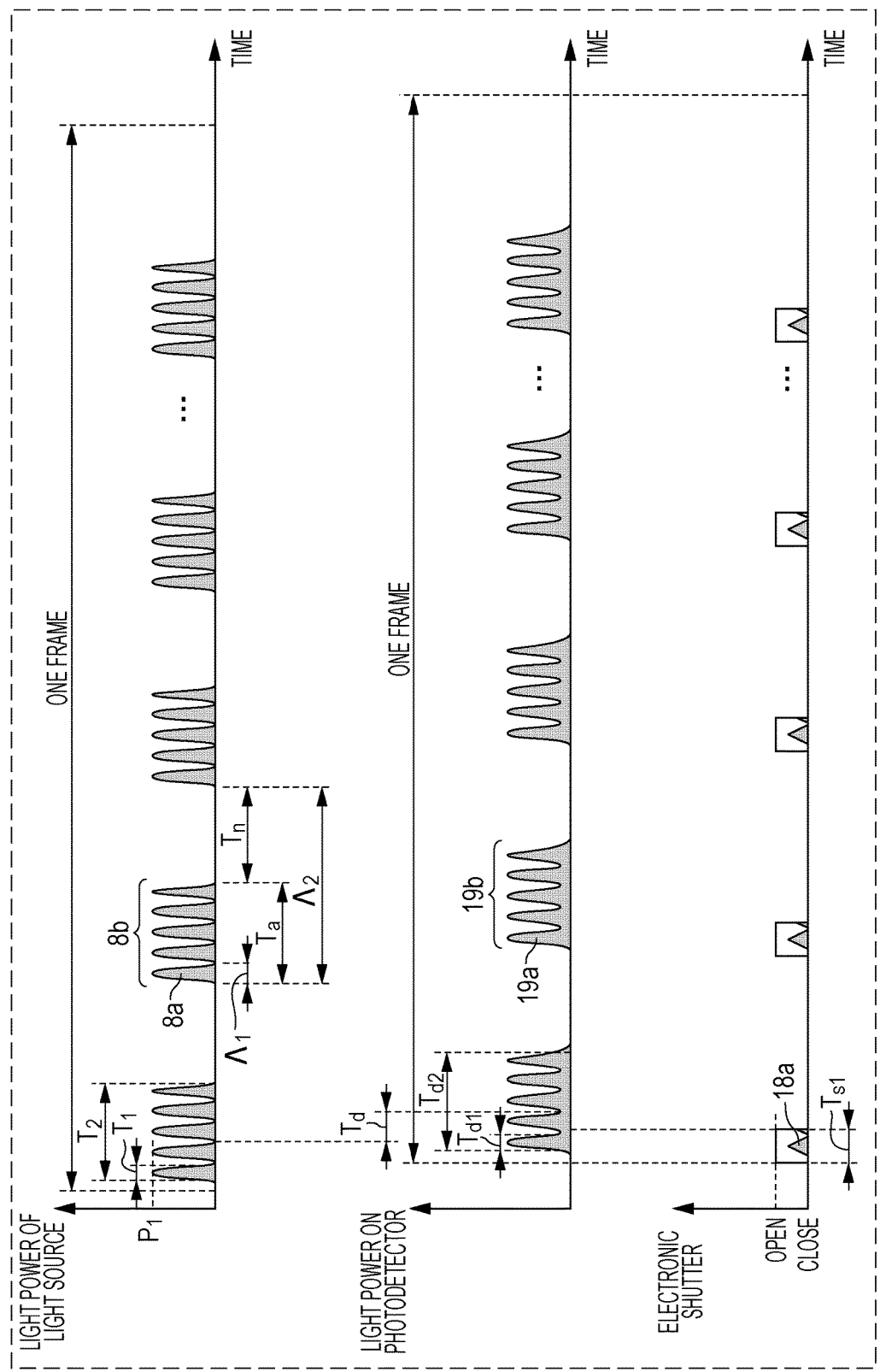

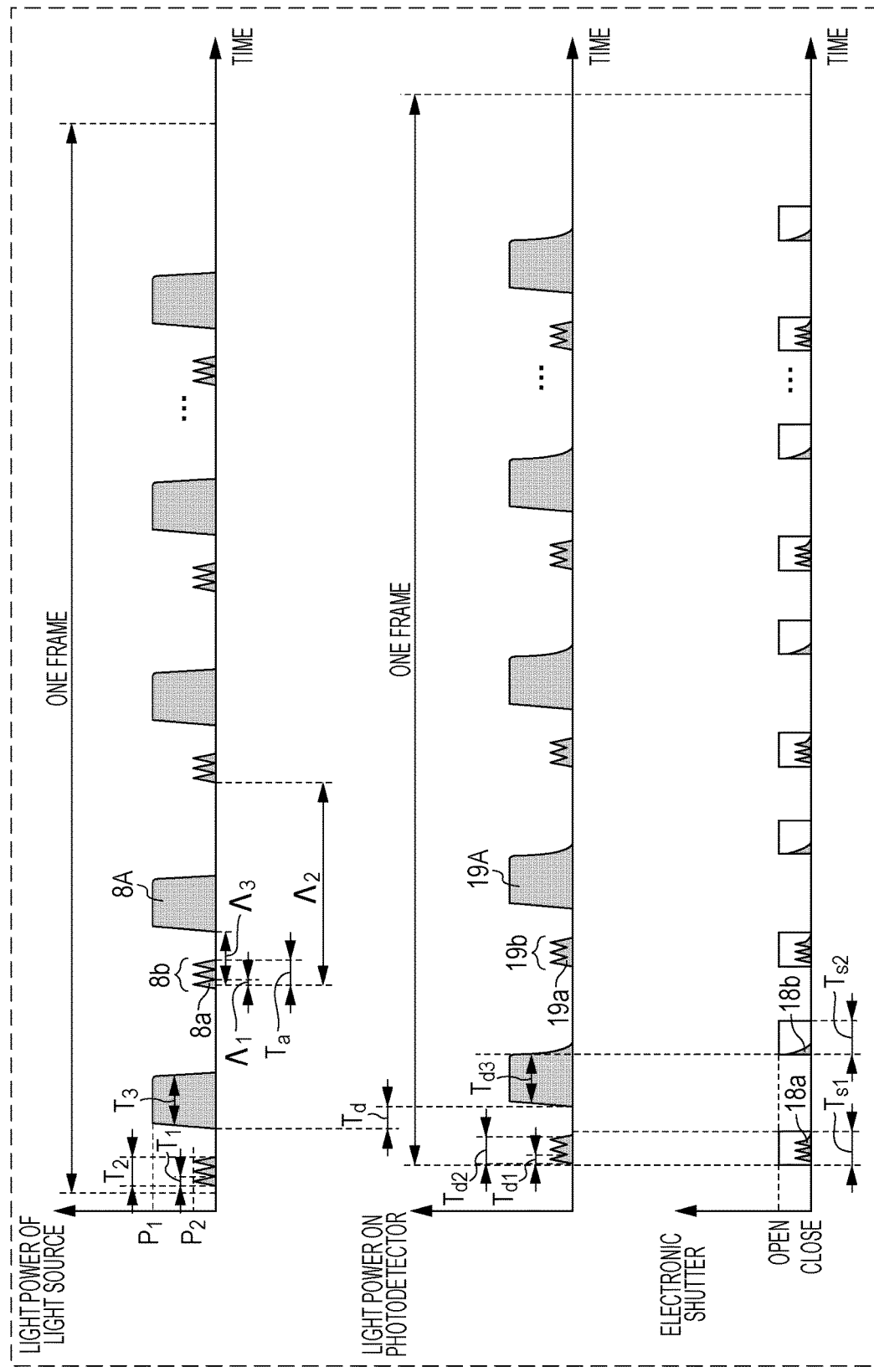

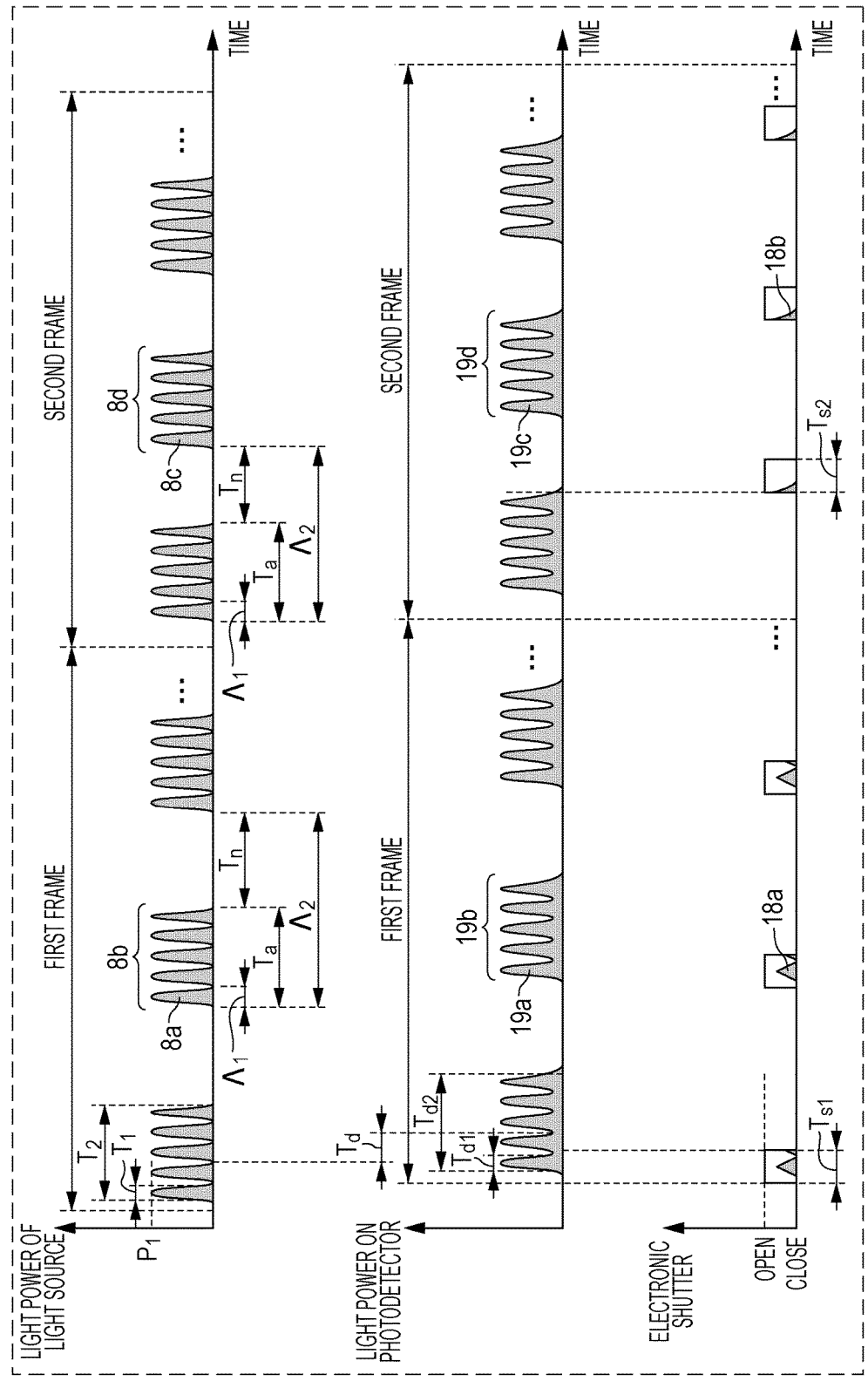

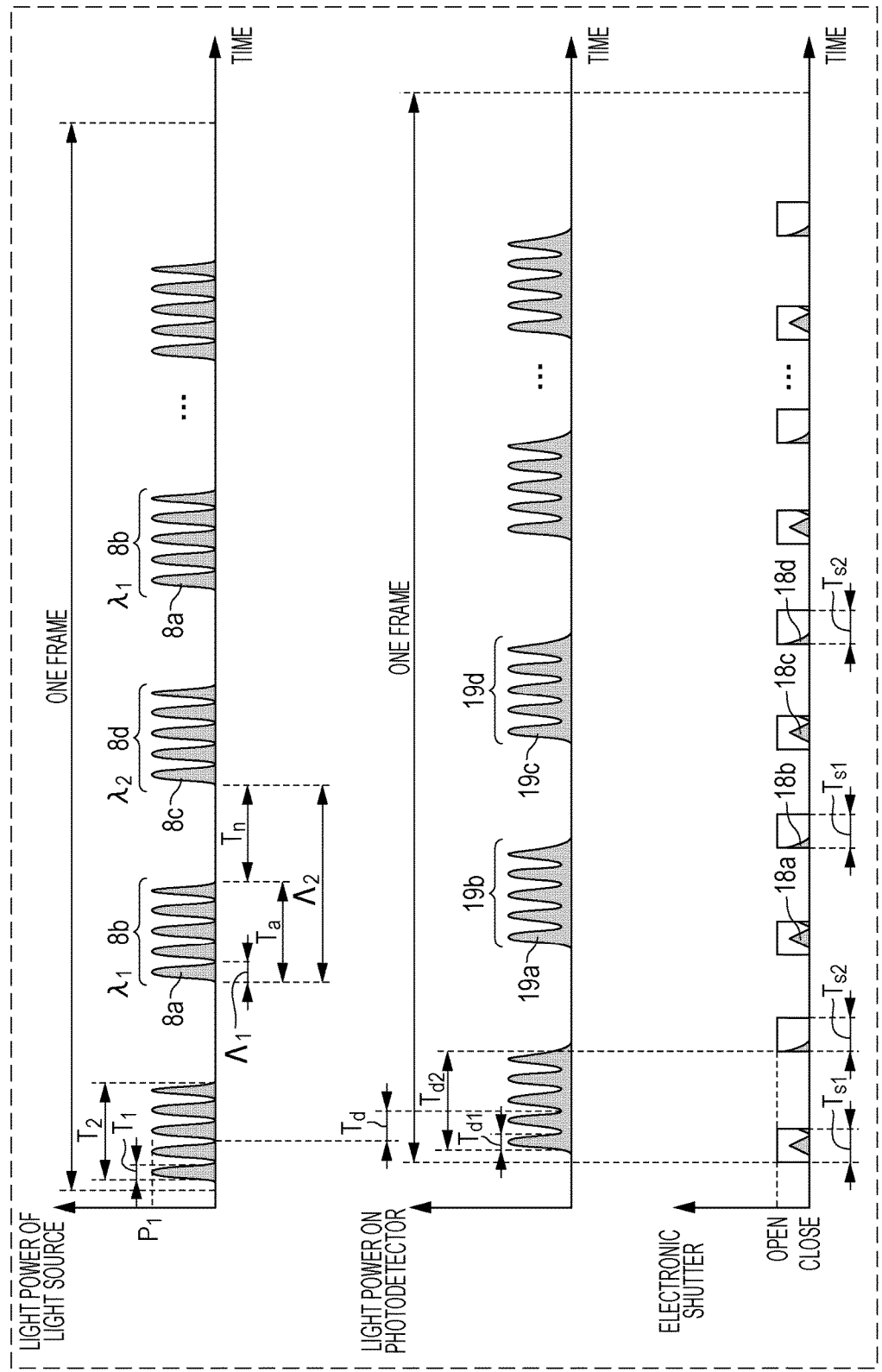

MEASURING DEVICE INCLUDING LIGHT SOURCE THAT EMITS AT LEAST ONE LIGHT PULSE GROUP, PHOTODETECTOR, AND CONTROL CIRCUIT

BACKGROUND

1. Technical Field

The present disclosure relates to a measuring device.

2. Description of the Related Art

As basic parameters for determining the health condition of a human, heart rate, blood flow volume, blood pressure, oxygen saturation, and the like are widely used.

For the acquisition of biological information, electromagnetic waves falling within a wavelength range of near infrared radiation, i.e. approximately 700 nm to approximately 2500 nm, are frequently used. Among them, near infrared rays of comparatively short wavelengths, e.g. approximately not longer than 950 nm, are especially frequently used. Such near infrared rays of short wavelengths have the property of being transmitted through body tissue such as muscles, fat, and bones at comparatively high transmittances. Meanwhile, such near infrared rays have the property of being easily absorbed into oxyhemoglobin ($HbO_2$) and deoxyhemoglobin (Hb) in the blood. As a biological information measuring method that involves the use of these properties, near infrared spectroscopy (hereinafter abbreviated as "NIRS") is known. Use of NIRS makes it possible to measure, for example, the amount of change in blood flow in the brain or the amounts of change in oxyhemoglobin concentration and deoxyhemoglobin concentration in the blood. It is also possible to estimate the state of activity of the brain on the basis of the amount of change in blood flow, the oxygen state of hemoglobin, or the like.

Japanese Unexamined Patent Application Publication No. 2007-260123 and Japanese Unexamined Patent Application Publication No. 2003-337102 disclose devices based on NIRS.

SUMMARY

In one general aspect, the techniques disclosed here feature a measuring device including: a light source that emits at least one light pulse group toward a target part of an object, the at least one light pulse group each including light pulses emitted sequentially; a photodetector that detects at least a part of at least one reflected light pulse group, the at least one reflected light pulse group including reflected light pulses sequentially returning from the target part; and a control circuit that controls the light source and the photodetector. The control circuit causes the light source to emit the at least one light pulse group within a first period. The control circuit causes the photodetector to extract a first component within the first period, the first component being a component of light included in at least a part of a leading reflected light pulse of the f reflected light pulses. The control circuit causes the photodetector to output a first electric signal corresponding to the first component.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram schematically showing examples of a time distribution (upper row) of light pulse groups, a time distribution (middle row) of a light power that is detected by the photodetector, and the timing and charge storage (lower row) of an electronic shutter according to Embodiment 1;

FIG. 7 is a diagram schematically showing a time distribution (upper row) of light pulse groups, a time distribution (middle row) of a light power that is detected by the photodetector, and the timing and charge storage (lower row) of the electronic shutter according to a first modification of Embodiment 1;

FIG. 8 is a diagram schematically showing a time distribution (upper row) of light pulse groups and single light pulses, a time distribution (middle row) of a light power that is detected by the photodetector, and the timing and charge storage (lower row) of the electronic shutter according to a second modification of Embodiment 1;

FIG. 9A is a diagram schematically showing a time distribution (upper row) of light pulse groups, a time distribution (middle row) of a light power that is detected by the photodetector, and the timing and charge storage (lower row) of an electronic shutter according to Embodiment 2;

FIG. 11 is a diagram schematically showing a time distribution (upper row) of light pulse groups, a time distribution (middle row) of a light power that is detected by the photodetector, and the timing and charge storage (lower row) of an electronic shutter according to Embodiment 3;

DETAILED DESCRIPTION

Figure 1A:
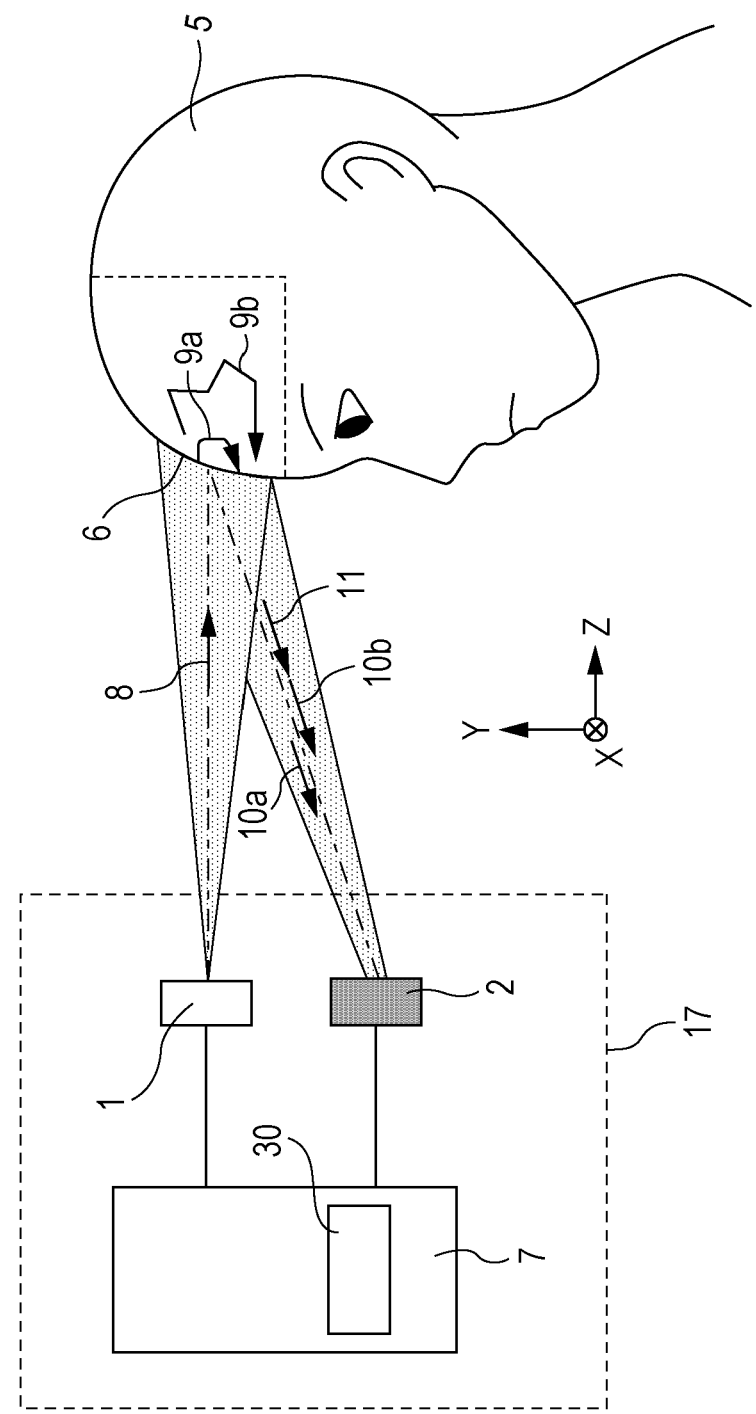
FIG. 1A is a schematic view for explaining a configuration of a biological measuring device according to Embodiment 1 of the present disclosure and the way in which a biological measurement is carried out.

Prior to a description of embodiments of the present disclosure, underlying knowledge forming the basis of the present disclosure is described.

Japanese Unexamined Patent Application Publication No. 2007-260123 discloses an endoscopic device based on NIRS. The endoscopic device disclosed in Japanese Unexamined Patent Application Publication No. 2007-260123 uses light pulses as illuminating light to observe blood flow information in blood vessels buried in body tissue covered with visceral fat. In so doing, by making an imaging timing later than the timing of incidence of a light pulse, imaging of intense noise light that returns temporally early is avoided. This improves the signal-to-noise ratio (S/N ratio) of signal light returning from a deep place in the body tissue.

Japanese Unexamined Patent Application Publication No. 2003-337102 discloses a biological activity measuring device based on NIRS. This measuring device includes a light source section that generates infrared light, a photodetection section that detects infrared light from a target part of a living body, and a controller. This measuring device measures brain functions in a non-contact manner.

The device disclosed in Japanese Unexamined Patent Application Publication No. 2003-337102 makes it possible to measure brain activity by means of NIRS. However, since light reflected by the target part includes intense noise light that returns temporally early, the S/N ratio of a signal that is detected is undesirably low.

It is conceivable that this problem may be solved by combining the technology of Japanese Unexamined Patent Application Publication No. 2007-260123 with the device of Japanese Unexamined Patent Application Publication No. 2003-337102. That is, it is conceivable that the influence of intense noise light that returns temporally early can be curbed by making the timing of detection of light later than the timing of incidence of a light pulse.

However, the inventors studied and found that, even with such measures being taken, it is difficult to make the S/N ratio sufficiently high. Emitted light having entered the brain scatteringly propagates through the brain. Detection of the light makes it possible to acquire information on blood flow in the brain. However, on the optical path from inside the brain to the device, i.e. on a return path, the light always passes through a region of distribution of blood flow near the surface of the living body, i.e. scalp blood flow. Therefore, information on scalp blood flow, as well as the information on brain blood flow, is greatly superimposed onto the light. As a result of that, accurate information on brain blood flow cannot be obtained simply by detecting the returning light. That is, with a method based on the combination of the conventional technologies, it is impossible to make the S/N ratio of a detection signal sufficiently high.

The inventors have found the foregoing problems and conceived of a novel measuring device.

The present disclosure encompasses measuring devices according to the following items.

Item 1

A measuring device according to Item 1 of the present disclosure includes: a light source that emits at least one light pulse group toward a target part of an object, the at least one light pulse group each including light pulses emitted sequentially;

a photodetector that detects at least a part of at least one reflected light pulse group, the at least one reflected light pulse group including reflected light pulses sequentially returning from the target part; and a control circuit that controls the light source and the photodetector.

The control circuit causes the light source to emit the at least one light pulse group within a first period, the control circuit causes the photodetector to extract a first component within the first period, the first component being a component of light included in at least a part of a leading reflected light pulse of the reflected light pulses, and the control circuit causes the photodetector to output a first electric signal corresponding to the first component.

An example of the object is a living body, food, or the like.

Item 2

In the measuring device according to Item 1, the control circuit may further cause the photodetector to extract a second component within the first period, the second component being a component of light included in a last reflected light pulse of the reflected light pulses during a falling period, the falling period being a period from a point in time at which the last reflected light pulse starts decreasing in light power to a point in time at which the last reflected light pulse finishes decreasing in light power, and the control circuit may cause the photodetector to output a second electric signal corresponding to the second component.

Item 3

In the measuring device according to Item 1, the control circuit may further cause the photodetector to extract a second component within a second period that is different from the first period, the second component being a component of light included in a last reflected light pulse of the f reflected light pulses during a falling period, the falling period being a period from a point in time at which the last reflected light pulse starts decreasing in light power to a point in time at which the last reflected light pulse finishes decreasing in light power, and the control circuit may cause the photodetector to output a second electric signal corresponding to the second component.

Item 4

In the measuring device according to Item 1, the at least one light pulse group may include a first light pulse group and a second light pulse group, the at least one reflected light pulse group may include a first reflected light pulse group and a second reflected light pulse group, the first reflected light pulse group may include first reflected light pulses, the second reflected light pulse group may include f second reflected light pulses, the control circuit may cause the light source to emit the first light pulse group and the second light pulse group within the first period, the second light pulse group may be emitted at a timing that is different from a timing at which the first light pulse group is emitted, the first component may be a component of light included in at least a part of a leading first reflected light pulse of the first reflected light pulses, the control circuit may further cause the photodetector to extract a second component within the first period, the second component being a component of light included in a last second reflected light pulse of the second reflected light pulses during a falling period, the falling period being a period from a point in time at which the last second reflected light pulse starts decreasing in light power to a point in time at which the last second reflected light pulse finishes decreasing in light power, and the control circuit may cause the photodetector to output a second electric signal corresponding to the second component.

Item 5

In the measuring device according to Item 1, the at least one light pulse group may include a first light pulse group and a second light pulse group, the at least one reflected light pulse group may include a first reflected light pulse group and a second reflected light pulse group, the first reflected light pulse group may include first reflected light pulses, the second reflected light pulse group may include second reflected light pulses, the control circuit may cause the light source to emit the first light pulse group within the first period, the first component may be a component of light included in at least a part of a leading first reflected light pulse of the first reflected light pulses, the control circuit may further cause the light source to emit the second light pulse group within a second period that is different from the first period, the control circuit may cause the photodetector to extract a second component within the second period, the second component being a component of light included in a last second reflected light pulse of the second reflected light pulses during a falling period, the falling period being a period from a point in time at which the last second reflected light pulse starts decreasing in light power to a point in time at which the last second reflected light pulse finishes decreasing in light power, and the control circuit may cause the photodetector to output a second electric signal corresponding to the second component.

Item 6

The measuring device according to any one of Items 2 to 5 may further include a signal processing circuit that generates blood flow information on the target part through a computation based on the first electric signal and the second electric signal.

Item 7

In the measuring device according to Item 6, the first electric signal may include blood flow information on a surface of the target part, the second electric signal may include the blood flow information on the surface of the target part and blood flow information on an interior of the target part, and the signal processing circuit may generates the blood flow information on the interior of the target part.

Item 8

In the measuring device according to Item 6 or 7, the photodetector may be an image sensor including photodetection cells arrayed two-dimensionally, and each of the plurality of photodetection cells may accumulate the first component as a first signal charge, accumulate the second component as a second signal charge, output, as the first electric signal, an electric signal corresponding to a total amount of the first signal charge, and output, as the second electric signal, an electric signal corresponding to a total amount of the second signal charge.

Item 9

In the measuring device according to Item 8, the control circuit may cause the image sensor to output a first image signal corresponding to a first two-dimensional distribution of the total amount of the first signal charge accumulated in the photodetection cells during a first period, a second image signal corresponding to a second two-dimensional distribution of the total amount of the second signal charge accumulated in the photodetection cells during a second period that is identical to or different from the first period, a third image signal corresponding to a third two-dimensional distribution of the total amount of the first signal charge accumulated in the photodetection cells during a third period preceding the first period, and a fourth image signal corresponding to a fourth two-dimensional distribution of the total amount of the second signal charge accumulated in the photodetection cells during a fourth period preceding the second period, and the signal processing circuit may receive the first to fourth image signals from the image sensor, generate a first difference image corresponding to a difference between the first image signal and the third image signal, and generate a second difference image corresponding to a difference between the second image signal and the fourth image signal.

Item 10

In the measuring device according to Item 9, $0.1 \leq M_1/M_2 \leq 10$ may be satisfied when the first difference image includes first pixels each of which has a pixel value exceeding a first threshold, the first pixels forming a first region, the second difference image includes second pixels each of which has a pixel value exceeding a second threshold, the second pixels forming a second region, $M_1$ is an average pixel value in a part of the first region that overlaps the second region, and $M_2$ is an average pixel value in a part of the second region that overlaps the first region.

Item 11

In the measuring device according to any one of Items 1 to 10, the at least one light pulse group may include a first light pulse group including light pulses having a wavelength of not shorter than 650 nm to shorter than 805 nm and a second light pulse group including light pulses having a wavelength of longer than 805 nm to not longer than 950 nm, and the control circuit may cause the light source to alternately emit the first light pulse group and the second light pulse group.

Item 12

In the measuring device according to any one of Items 1 to 11, each of the light pulses may have a length of time of not shorter than 0.5 nanosecond to shorter than 3.0 nanoseconds.

Item 13

In the measuring device according to any one of Items 1 to 11, each of the light pulses may have a length of time of not shorter than 0.5 nanosecond to shorter than 5.0 nanoseconds.

Item 14

In the measuring device according to any one of Items 1 to 13, the light source may be a semiconductor laser, and by supplying the light source with a driving current on which a high-frequency component has been superimposed, the control circuit may cause the light source to emit the at least one light pulse group.

Item 15

In the measuring device according to any one of Items 1 to 13, the light source may be a self-oscillation laser.

Item 16

A measuring device according to Item 16 includes: a light source that emits at least one light pulse group and at least one second light pulse toward a target part of an object, the at least one light pulse group each including first light pulses emitted sequentially; a photodetector that detects at least a part of at least one reflected light pulse group and at least a part of at least one second reflected light pulse returning from the target part, the at least one reflected light pulse group including first reflected light pulses sequentially returning from the target part; and a control circuit that controls the light source and the photodetector.

The control circuit causes the light source to emit the at least one light pulse group within a first period, the control circuit causes the photodetector to extract a first component within the first period, the first component being a component of light included in at least the part of the at least one reflected light pulse group, the control circuit causes the photodetector to output a first electric signal corresponding to the first component, the control circuit causes the light source to emit the at least one second light pulse at a timing within the first period or within a second period that is different from the first period, the timing being different from a timing at which the at least one light pulse group is emitted, the control circuit causes the photodetector to extract a second component within the first period or within the second period, the second component being a component of light included in the at least one second reflected light pulse during a falling period, the falling period being a period from a point in time at which the at least one second reflected light pulse starts decreasing in light power to a point in time at which the at least one second reflected light pulse finishes decreasing in light power, and the control circuit causes the photodetector to output a second electric signal corresponding to the second component.

Item 17

In the measuring device according to Item 16, a light power of the at least one second light pulse may be greater than a light power of each of the first light pulses.

In the present disclosure, all or some of the circuits, units, devices, members, or sections or all or some of the functional blocks in the block diagrams may be implemented as one or more of electronic circuits including, but not limited to, a semiconductor device, a semiconductor integrated circuit (IC), or an LSI (large scale integration). The LSI or IC can be integrated into one chip, or also can be a combination of multiple chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or some of the functions or operations of the circuits, units, devices, members, or sections are implemented by executing software. In such a case, the software is recorded on one or more non-transitory recording media such as a ROM, an optical disk, or a hard disk drive, and when the software is executed by a processor, the software causes the processor together with peripheral devices to execute the functions specified in the software. A system or device may include such one or more non-transitory recording media on which the software is recorded and a processor together with necessary hardware devices such as an interface.

In the following, embodiments of the present disclosure are more specifically described. Note, however, that an unnecessarily detailed description may be omitted. For example, a detailed description of a matter that has already been well known and a repeated description of substantially identical configurations may be omitted. This is intended to prevent the following description from becoming unnecessarily redundant and facilitate understanding of persons skilled in the art. It should be noted that the inventors provide the accompanying drawings and the following description so that persons skilled in the art can sufficiently understand the present disclosure, and do not intend to thereby limit the subject matters recited in the claims. In the following description, identical or similar constituent elements are given the same reference signs.

In the following, embodiments are described with reference to the drawings.

Embodiment 1

Figure 1B:
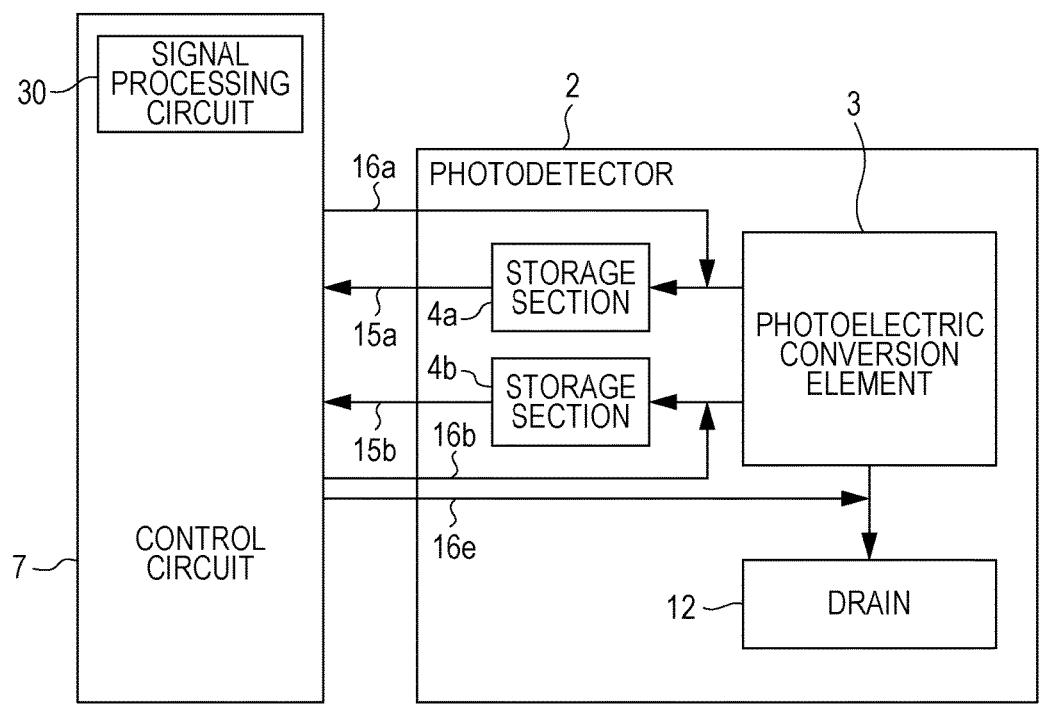
FIG. 1B is a diagram schematically showing an internal configuration of a photodetector according to Embodiment 1 of the present disclosure and the flow of signals.

FIG. 1A is a schematic view for explaining a configuration of a biological measuring device 17 according to Embodiment 1 of the present disclosure and the way in which a biological measurement is carried out. FIG. 1B is a diagram schematically showing an internal configuration of a photodetector 2 according to Embodiment 1 of the present disclosure and the flow of signals.

The biological measuring device 17 according to Embodiment 1 includes a light source 1, the photodetector 2, and a control circuit 7 that controls the light source 1 and the photodetector 2.

The light source 1 and the photodetector 2 are arranged side by side. The light source 1 emits light toward a target part 6 of a subject 5. The photodetector 2 detects light emitted from the light source 1 and reflected by the target part 6. The control circuit 7 controls the emission of light by the light source 1 and the detection of light by the photodetector 2. The biological measuring device 17 according to Embodiment 1 includes a signal processing circuit 30 that processes electric signals (hereinafter simply referred to as "signals") that are outputted from the photodetector 2. The signal processing circuit 30 performs computations based on a plurality of signals outputted from the photodetector 2 and thereby generates information about blood flow in the interior of the target part 6.

The target part 6 according to Embodiment 1 is a forehead part of the subject 5. Information on brain blood flow can be acquired by irradiating the forehead part with light and detecting the resulting scattered light. The "scattered light" includes reflected scattered light and transmitted scattered light. In the following description, the reflected scattered light is sometimes simply referred to as "reflected light".

Present in the interior of the forehead, which is the target part 6, are the scalp (approximately 3 to 6 mm thick), the skull (approximately 5 to 10 mm thick), the cerebrospinal fluid layer (approximately 2 mm thick), and the brain tissue, starting from the surface. The ranges of thicknesses in parentheses mean that there are differences between individuals. Blood vessels are present in the scalp and in the brain tissue. Therefore, blood flow in the scalp is called "scalp blood flow", and blood flow in the brain tissue is called "brain blood flow". In a brain function measurement according to Embodiment 1, a measurement object is a target part where there are blood flow distributions both near the surface of and in the interior of the scalp.

A living body is a scatterer. A portion of light 8 emitted toward the target part 6 returns as directly-reflected light 10a to the biological measuring device 17. Another portion of the light enters the interior of the target part 6 and gets diffused, and a portion of it is absorbed. The light having entered the interior of the target part 6 turns into internally-scattered light 9a including information on blood flow near the surface that is present approximately 3 to 6 mm deep in the scalp from the surface, i.e. scalp blood flow, internally-scattered light 9b including information on blood flow that is present in a range of depth of approximately 10 to 18 mm from the surface, i.e. brain blood flow, or the like. The internally-reflected light 9a and the internally-reflected light 9b return to the biological measuring device 17 as reflected scattered light 10b from near the surface and as reflected scattered light 11 from the interior, respectively. The directly-reflected light 10a, the reflected scattered light 10b from near the surface, and the reflected scattered light 11 from the interior are detected by the photodetector 2.

It takes the shortest time, the second shortest time, and the longest time for the directly-reflected light 10a, the reflected scattered light 10b from near the surface, and the reflected scattered light 11 from the interior, respectively, to arrive at the photodetector 2 after being emitted from the light source 1. Among them, the component required to be detected at a high S/N ratio is the reflected scattered light 11 from the interior, which has the information on brain blood flow.

It should be noted that the transmitted scattered light, as well as the reflected scattered light, may be used in carrying out a biological measurement other than a brain blood flow measurement. In a case where information on blood other than brain blood flow is acquired, the target part 6 may be a part other than the forehead (e.g. an arm, a leg, or the like). In the following description, unless otherwise noted, the target part 6 is the forehead. The subject 5 is a human, but may alternatively be a non-human animal having skin and having a hairless part. The term "subject" as used herein means specimens in general including such animals.

The light source 1 emits light of, for example, not shorter than 650 nm to not longer than 950 nm. This wavelength range is included in a wavelength range of red to near infrared radiation. The aforementioned wavelength range is called "biological window" and known to be low in absorptance in the body. The light source 1 according to Embodiment 1 is described as one that emits light falling within the aforementioned wavelength range, but light falling within another wavelength range may be used. The term "light" as used herein means not only visible light but also infrared radiation.

In a visible light region of shorter than 650 nm, absorption by hemoglobin in the blood is high, and in a wavelength range of longer than 950 nm, absorbance by water is high. Meanwhile, in a wavelength range of not shorter than 650 nm to not longer than 950 nm, the absorption coefficients of hemoglobin and water are comparatively low and the scattering coefficients of hemoglobin and water are comparatively high. Therefore, light falling within the wavelength range of not shorter than 650 nm to not longer than 950 nm is subjected to strong scattering after entering the body and returns to the body surface. This makes it possible to efficiently acquire information on the interior of the body. Accordingly, Embodiment 1 mainly uses light falling within the wavelength range of not shorter than 650 nm to not longer than 950 nm.

The light source 1 may be a laser light source, such as a laser diode (LD), that repeatedly emits a light pulse. In a case where the subject 5 is a human as in the case of Embodiment 1, the impact of the light 8 on the retina is considered. In a case where a laser light source is used as the light source 1, a laser light source that satisfies Class 1 of laser safety standards devised by each country is selected, for example. In a case where Class 1 is satisfied, light of such low illuminance that the accessible emission limit AEL falls below 1 mW is emitted toward the part being test 6 of the subject 5. Since the light is of low illuminance, the sensitivity of the photodetector 2 is not enough in many cases. In that case, a light pulse is repeatedly emitted. It should be noted that the light source 1 per se does not need to satisfy Class 1. For example, light is diffused or attenuated by placing an element such as a diffusing plate or an ND filter between the light source 1 and the target part 6. In this way, Class 1 of the laser safety standards may be satisfied.

An optical element such as a lens may be provided on an emission surface of the light source 1 to adjust the degree of divergence of the light 8. Furthermore, an optical element such as a lens may be provided on a light-receiving surface side of the photodetector 2 to adjust the rate of extraction of reflected scattered light that is received.

The light source 1 is not limited to a laser light source but may be another type of light source such as a light-emitting diode (LED). Widely useable examples of the light source 1 include a semiconductor laser, a solid laser, a fiber laser, a super luminescent diode, an LED, and the like.

The light source 1 can start and stop the emission of a light pulse and change light powers in accordance with instructions from the control circuit 7. This allows almost any light pulse to be generated from the light source 1.

The photodetector 2 detects light returning from the target part 6. The photodetector 2 may include a single photodetection element or may include a plurality of photodetection elements arrayed one-dimensionally or two-dimensionally. FIG. 1B schematically shows a configuration of one photodetection element in the photodetector 2. The photodetection element of the photodetector 2 in this example includes a photoelectric conversion element 3 that generates signal charge corresponding to the amount of light received, a plurality of storage sections 4a and 4b in which signal charge is accumulated, and a drain 12 through which signal charge is discharged. The photoelectric conversion element 3 may include, for example, a photodiode. Signal charge produced by the photoelectric conversion element 3 is accumulated in either of the plurality of storage sections 4a and 4b or discharged through the drain 12. The timings of signal storage and discharge are controlled by the control circuit 7 and an internal circuit of the photodetector 2. The internal circuit of the photodetector 2 involved in this control is herein sometimes referred to as "electronic shutter".

The photodetector 2 may be an image sensor having sensitivity to light in a wavelength range including wavelengths of light that is emitted from the light source 1. An example of such an image sensor may be a CCD or CMOS image sensor. Use of an image sensor makes it possible to acquire information on a two-dimensional intensity distribution of light. In a case where the photodetector 2 is an image sensor, the photodetector 2 includes a plurality of photodetection cells arrayed two-dimensionally. As shown, for example, in FIG. 1B, each of the photodetection cells includes constituent elements such as the photoelectric conversion element 3 and the storage sections 4a and 4b.

As will be mentioned later, use of the photodetector 2 such as an image sensor makes it possible to generate an image that indicates a state of brain blood flow. One image may be generated by repeating light emission and signal charge storage more than once within one frame period. A moving image can be generated by repeatedly executing such image generation every predetermined frame period.

In order to quantify the light amounts of the directly-reflected light 10a, the reflected scattered light 10b, and the reflected scattered light 11, the inventors ran a simulation of a light pulse response assuming, as the target part 6, a phantom mimicking the head of a typical Japanese. Specifically, the inventors calculated through a Monte Carlo analysis a time distribution of a light power, i.e. a light pulse response, that is detected by the photodetector 2 in a case where a light pulse is emitted toward the target part 6 located at a distance of, for example, 15 cm from the light source 1.

Figure 2A:
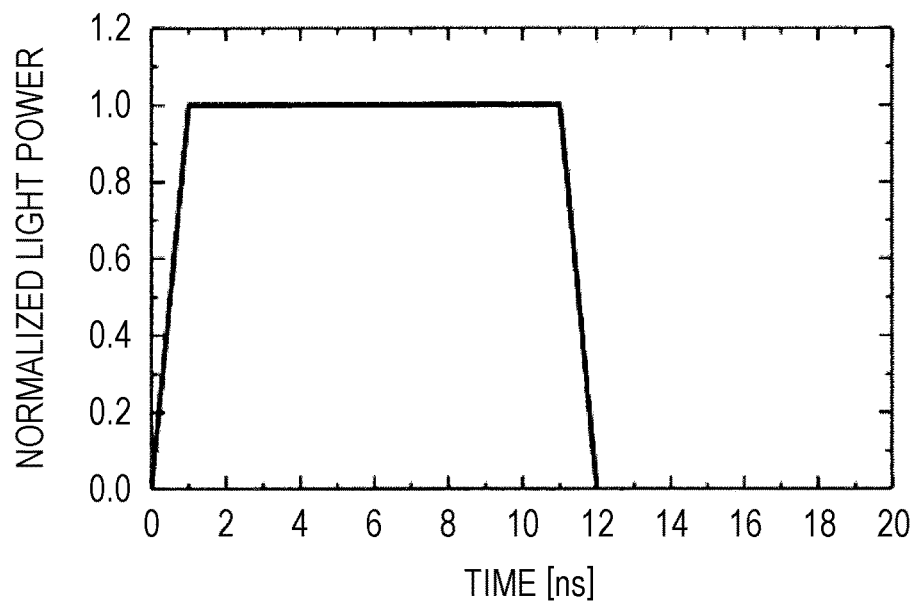
FIG. 2A is a diagram showing an example of a time distribution of a single light pulse that is emitted light.

FIG. 2A is a diagram showing an example of a time distribution of a single light pulse that is emitted light. In this example, the light pulse has a wavelength λ of 850 nm and a full width at half maximum of 11 ns. This light pulse has a typical trapezoidal shape whose rising and falling times are each 1 ns. Assume that the emission of the single light pulse starts at a time t=0 and completely stops at t=12 ns.

Since the velocity of light c is 300000 km/s and the distance from the light source 1 to the target part 6 is 15 cm, the time t from the emission of the light 8 to the arrival of the light 8 at the surface of the target part 6 is expressed as t=0.5 ns. The time it takes for the light 8 to arrive at a surface of the photodetector 2 after being directly reflected by the surface of the target part 6 and turning into the directly-reflected light 10a is expressed as t=1 ns. Therefore, the time $T_d$ it takes for the light to be detected on the photodetector 2 is expressed as $T_d \geq 1$ ns.

The biological measuring device 17 measures the amount of change in light amount of the reflected scattered light 11 from the interior of the target part 6 on the basis of changes in oxyhemoglobin concentration and deoxyhemoglobin concentration in the brain blood flow. The brain tissue has an absorber whose absorption coefficient and scattering coefficient vary according to changes in brain blood flow. In a stationary state, it is possible to model the interior of the brain as uniform brain tissue and conduct a Monte Carlo analysis. The term "changes in blood flow" as used herein means temporal changes in blood flow. The term "stationary state" here means a state where the subject is comparatively stable in brain activity and there are no sudden time fluctuations in brain activity of the subject.

Figure 2B:
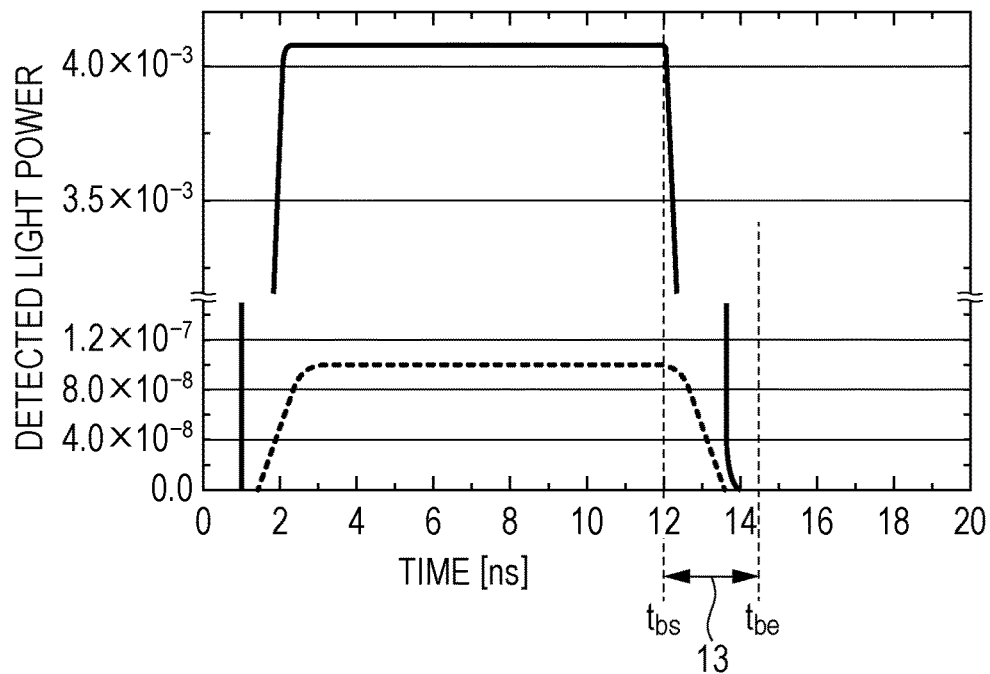
FIG. 2B is a diagram showing time distributions of a total light power (solid line) of the single light pulse in a stationary state and a power (dashed line) of light having passed through a region of change in brain blood flow.
Figure 2C:
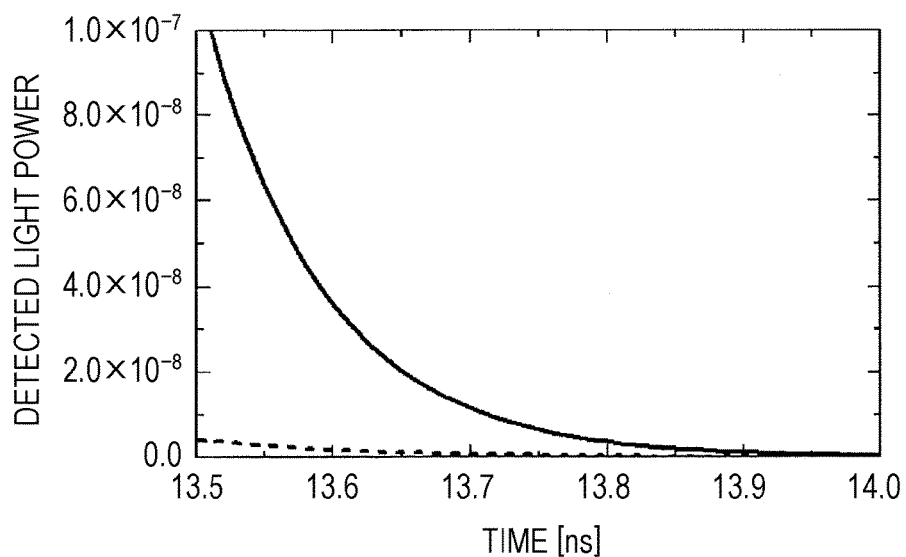
FIG. 2C is a diagram showing time distributions, during a falling period, of the total light power (solid line) of the single light pulse in the stationary state and the power (dashed line) of the light having passed through the region of change in brain blood flow.
Figure 2D:
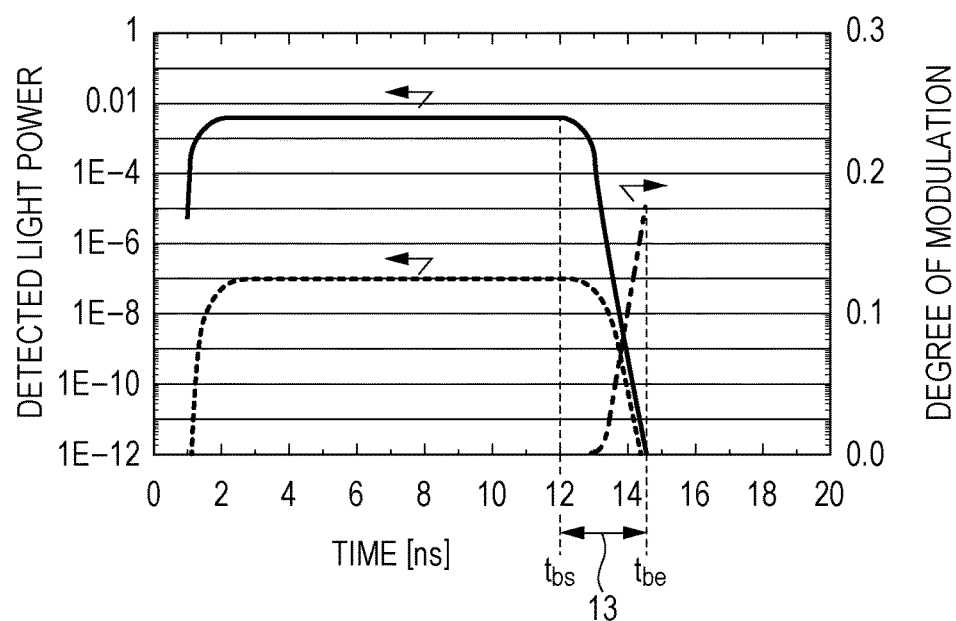
FIG. 2D is a diagram showing time distributions of the total light power (solid line) of the single light pulse in the stationary state, the power (dashed line) of the light having passed through the region of change in brain blood flow, and a degree of modulation (chain line)

FIG. 2B is a diagram showing time distributions of a total light power (solid line) of the single light pulse in a stationary state and a power (dashed line) of light having passed through a region of change in brain blood flow. FIG. 2C is a diagram showing time distributions, during a falling period, of the total light power (solid line) of the single light pulse in the stationary state and the power (dashed line) of the light having passed through the region of change in brain blood flow. FIG. 2D is a diagram showing time distributions of the total light power (solid line) of the single light pulse in the stationary state, the power (dashed line) of the light having passed through the region of change in brain blood flow, and a degree of modulation (chain line). The degree of modulation means a value obtained by dividing, by the total amount of light in the stationary state, the amount of light having passed through the region of change in brain blood flow. In each of FIGS. 2B and 2C, the vertical axis is expressed by a linear display, and in FIG. 2D, the vertical axis is expressed by a logarithmic display.

The amount of light having passed through the region of change in brain blood flow, which is included in the total amount of light that is detected by the photodetector 2, is only approximately $2 \times 10^{-5}$. That is, in a case where a light pulse is emitted, the total amount of light is detected by the photodetector 2, and a change therein is detected, a component included in the light amount thus detected that indicates changes in brain blood flow is so small as to be negligible. On the other hand, the directly-reflected light 10a is constant in light amount and has a reflectance of, for example, approximately 4%. This makes it possible to detect changes in light amount of the directly-reflected light 10a from near the surface, i.e. changes in scalp blood flow.

Let it be assumed that $t_{bs}$ is the time at which the light power starts to decrease on the photodetector 2 and $t_{be}$ is the time at which the light power completely decreases to a noise level. As shown in FIG. 2D, it is found that the proportion of signals that indicate changes in brain blood flow becomes higher in a falling period 13 of light $t_{bs} \leq t \leq t_{be}$. As the second half of the falling period 13 of light passes, the light amount decreases and noise increases accordingly. However, the degree of modulation becomes higher. Of the light falling period 13 of light $t_{bs} \leq t \leq t_{be}$, the amount of light at and after t=13.5 ns, for example, is approximately 1/100 of the total amount of light detected. In a case where light arriving during the period 13 is detected with use of the function of an electronic shutter of the photodetector 2, the proportion of the light having passed through the region of change in brain blood flow increases to 7% of the total amount of light detected at and after t=13.5 ns. This makes it possible to sufficiently acquire signals that indicate changes in brain blood flow. Without use of the electronic shutter, the proportion of changes in brain blood flow is approximately $2\times10^{-5}$.

Therefore, signals that indicate changes in brain blood flow can be detected by using the photodetector 2 to receive a component of the reflected scattered light 11 included in the falling period 13 of light returning from the target part 6 and detect changes in light amount thereof.

Blood flow information may be acquired by using, instead of a single light pulse such as that shown in FIGS. 2A to 2D, a light pulse group including a plurality of light pulses arranged continuously.

Figure 3A:
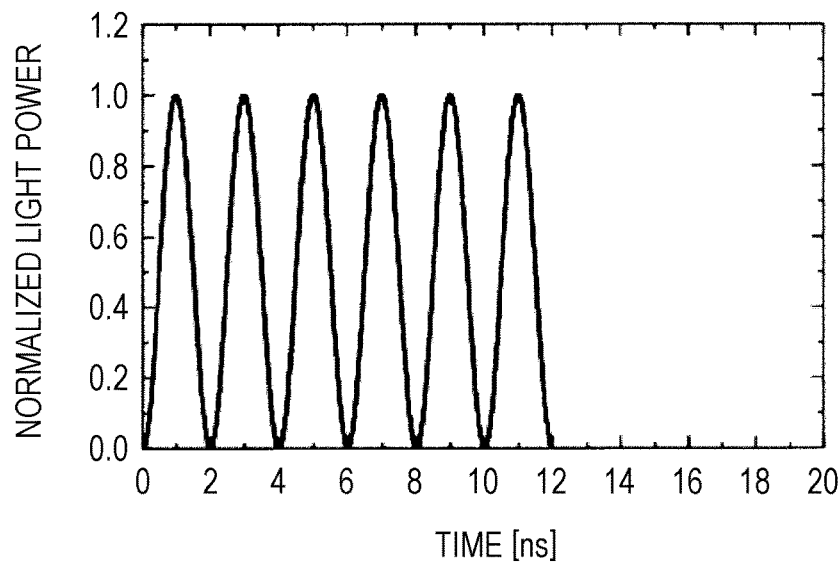
FIG. 3A is a diagram showing an example of a time distribution of a light pulse group that is emitted light.

FIG. 3A is a diagram showing an example of a time distribution of a light pulse group that is emitted light. In the example shown in FIG. 3A, the light pulse group includes six light pulses each having a full width at half maximum of 1 nanosecond. The number of light pulses that are included in one light pulse group does not need to be 6 and is not limited to a particular number. Each of the pulses may have a full width at half maximum of, for example, not shorter than 0.5 nanosecond to not longer than 5.0 nanoseconds. In the example shown in FIG. 3A, the emission of the light pulse group starts at the time t=0 and completely stops at a time t=12 ns.

In a case where the light source 1 is a semiconductor laser light source, the control circuit 7, by supplying the light source 1 with a driving current on which a high-frequency component has been superimposed, can cause the light source 1 to emit one or more light pulse groups. In this case, the control circuit 7 may include a separate driving circuit for supplying a high-frequency current. In a case where such driving based on high-frequency superimposition is performed, a reduction in speckle noise can be achieved as will be mentioned later. The light source 1 may be a self-oscillation laser light source. In that case, the control circuit 7 may supply the light source 1 with a DC driving current.

Figure 3B:
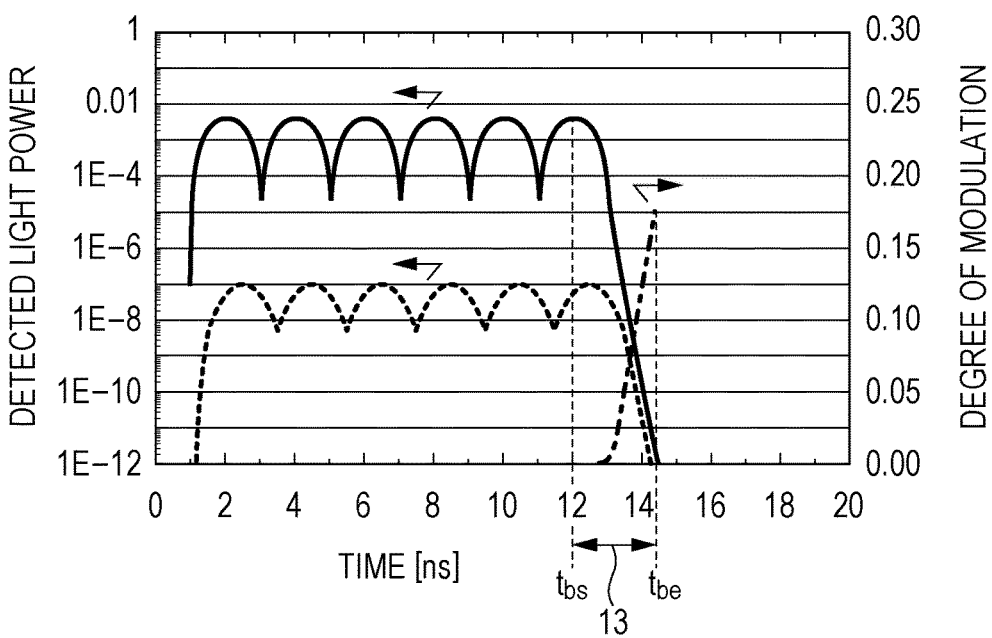
FIG. 3B is a diagram showing examples of time distributions of a total light power (solid line) of the light pulse group, a power (dashed line) of light having passed through a region of change in brain blood flow, and a degree of modulation (chain line)

FIG. 3B is a diagram showing examples of time distributions of a total light power (solid line) of the light pulse group, a power (dashed line) of light having passed through a region of change in brain blood flow, and a degree of modulation (chain line). The inventors found that, in the example shown in FIG. 3B, a degree of modulation which is equal to or higher than that of the example shown in FIG. 2D can be achieved. A light pulse group has the following advantage over a single light pulse. Irradiation of the target part 6 with a single light pulse leads to the appearance of a pattern of bright and dark spots in the area being irradiated. This is called speckle noise, which causes deterioration in measurement accuracy. On the other hand, irradiation of the target part 6 with a light pulse group leads to a reduction in such speckle noise.

The following describes an example of a biological measuring method based on the aforementioned principle of measurement of changes in scalp blood flow and brain blood flow.

FIG. 4 is a diagram schematically showing examples of a time distribution (upper row) of light pulse groups 8b, a time distribution (middle row) of a light power that is detected by the photodetector 2, and the timing and charge storage (lower row) of an electronic shutter.

In this example, the control circuit 7 causes the light source 1 to emit a plurality of light pulse groups 8b within one frame period and causes the photodetector 2 to detect a first component within one frame period. The first component is a component of light including at least a part of a leading reflected light pulse 19a included in each reflected light pulse group 19b returning from the target part 6 due to a corresponding one of the light pulse groups 8b. After that, the control circuit 7 causes the photodetector 2 to output a first electric signal corresponding to the first component. The first electric signal represents a total amount of the first component accumulated within one frame period. The control circuit 7 further causes the photodetector 2 to detect a second component within one frame period. The second component is a component of light included in the falling period 13 of the last reflected light pulse included in each reflected light pulse group 19b. After that, the control circuit 7 causes the photodetector 2 to output a second electric signal corresponding to the second component. The second electric signal represents a total amount of the second component accumulated within one frame period.

As shown in the upper row of FIG. 4, the light source 1 emits a light pulse group 8b more than once within one frame period. There is a pause period $T_n$ between two consecutive light pulse groups 8b. The leading light pulse 8a in each of the light pulse groups 8b has a pulse width $T_1$ and a maximum light power value $P_1$. Each of the light pulse groups 8b has a pulse width $T_2$. The term "pulse width" as used herein means the full width at half maximum of a pulse waveform. Each of the light pulse groups 8b in this example includes five light pulses.

As shown in the middle row of FIG. 4, reflected light pulses 19a returning from the target part 6 due to the leading light pulses 8a each have a pulse width $T_{d1}$, which is substantially the same as $T_1$. Similarly, reflected light pulse groups 19b returning from the target part 6 due to the light pulse groups 8b each have a pulse width $T_{d2}$, which is substantially the same as $T_2$. As shown in the middle row of FIG. 4, the reflected light pulses 19a have shapes that become slightly wider toward the skirts due to the occurrence of time delays under the influence of internal scattering.

The photodetector 2 detects therethrough the first component, which includes a reflected light pulse 19a returning from the target part 6 due to a leading light pulse 8a, and the second component, which is included in the falling period 13 of the last reflected light pulse in a reflected light pulse group 19b returning from the target part 6 due to a light pulse group 8b. More specifically, the photodetector 2 performs photoelectric conversion trough the photoelectric conversion element 3 shown in FIG. 1B and accumulates a first signal charge 18a and a second signal charge 18b in the storage sections 4a and 4b, respectively.

In a case where the target part 6 is the forehead of a human, a light pulse group 8b may enter the eyes. For this reason, a light pulse group 8b may be emitted, for example, with such a low power as to satisfy Class 1. In order to secure such a sufficient amount of light that the photodetector 2 can detect, a light pulse group 8b may be repeatedly emitted. Let it be assumed that $\Lambda_1$ is the time from the beginning to end of emission of a leading light pulse 8a, $T_a$ is the time from the beginning to end of emission of a light pulse group 8b, and $T_n$ is the time from the end of emission of a light pulse group 8b to the beginning of emission of the next light pulse group 8b. In the example shown in FIG. 4, $T_a=5\Lambda_1$. In an example, a light pulse group 8b is repeatedly emitted approximately 10000 times to 1000000 times in a time cycle $\Lambda_2=T_a+T_n$ of approximately 55 ns to 110 ns.

The photodetector 2 in this example is an image sensor that can measure a two-dimensional distribution of light power. The photodetector 2 generates a frame every certain frame period. One frame is composed by the charge accumulated in the storage sections 4a and 4b of each of the photodetection elements of the photodetector 2. A frame is image data that represents a state of brain blood flow in the target part 6. By arranging a plurality of frames on a time-series basis, a moving image that indicates temporal changes in state of brain blood flow can be composed.

It is possible, without imposing a Class 1 limitation, to measure biological information other than brain blood flow with use of a high light power or measure biological information with use of a highly sensitive photodetector such as an avalanche photodiode. In that case, the emission of a light pulse group 8b does not necessarily need to be repeated more than once within one frame period. Biological information may be detected by irradiating the target part 6 only once with a light pulse group 8b within one frame period.

The photodetector 2 according to Embodiment 1 includes the electronic shutter, which switches between storing signal charge and not storing signal charge, and the plurality of storage sections 4a and 4b. The electronic shutter is a circuit that controls the storage and discharge of signal charge generated by the photoelectric conversion element 3.

With continued reference to FIG. 1B, an example of operation of the photodetector 2 is described. The photoelectric conversion element 3 photoelectrically converts the first component, which includes a reflected light pulse 19a returning from the target part 6 due to the leading light pulse 8a in each of the light pulse groups 8b. After that, in reaction to control signals 16a, 16b, and 16e from the control circuit 7, the photodetector 2 selects the storage section 4a and accumulates the first signal charge 18a. The first signal charge 18a is accumulated for a period of time $T_{S1}$ of, for example, 11 to 22 ns. After the period of time $T_{S1}$ has elapsed, in accordance with the control signals 16a, 16b, and 16e from the control circuit 7, the photodetector 2 selects the drain 12 and releases an electric charge from the photoelectric conversion element 3.

Similarly, the photoelectric conversion element 3 photoelectrically converts the second component, which is included in the falling period 13 of the last reflected light pulse in a reflected light pulse group 19b returning from the target part 6 due to a light pulse group 8b. After that, in reaction to the control signals 16a, 16b, and 16e from the control circuit 7, the photodetector 2 selects the other storage section 4b and accumulates the second signal charge 18b. The second signal charge 18b is accumulated for a period of time $T_{S2}$ of, for example, 11 to 22 ns. After the period of time $T_{S2}$ has elapsed, in accordance with the control signals 16a, 16b, and 16e from the control circuit 7, the photodetector 2 selects the drain 12 and releases an electric charge from the photoelectric conversion element 3.

Therefore, within one frame period, the first component, which includes a reflected light pulse 19a returning from the target part 6 due to the leading light pulse 8a in each of the light pulse groups 8b, is accumulated as one frame of the first signal charge 18a in the storage section 4a. After the end of one frame period, the first signal charge 18a is outputted as a first electric signal 15a to the control circuit 7. The first electric signal 15a mainly includes the information on scalp blood flow.

On the other hand, within one frame period, the second component, which is included in the falling period 13 of the last reflected light pulse in a reflected light pulse group 19b returning from the target part 6 due to each of the light pulse groups 8b, is accumulated as one frame of the second signal charge 18b in the storage section 4b. After the end of one frame period, the second signal charge 18b is outputted as a second electric signal 15b to the control circuit 7. The second electric signal 15b includes the information on scalp blood flow at a comparatively high rate as well as the information on brain blood flow.

After the emission of a plurality of light pulse groups 8b, ambient noise may be measured by keeping the electronic shutter open and closed for the same length of time and the same number of times in the absence of light emission. The S/N ratios of the signals can be improved by subtracting the value of the ambient noise from each of the signal values. $T_{S1}$ and $T_{S2}$ may be the same as or different from each other. If $T_{S1}=T_{S2}$, it is only necessary to measure the ambient noise once by keeping the electronic shutter open for the duration of $T_{S1}$. This makes it possible to omit to carry out a second measurement of the ambient noise by keeping the electronic shutter open for the duration of $T_{S2}$.

As mentioned above, the photodetector 2 according to Embodiment 1 may be an image sensor including, for each pixel, a photoelectric conversion element 3, storage sections 4a and 4b, and an electronic shutter that switches between storing signal charge and not storing signal charge in the storage sections 4a and 4b. In this case, the image sensor includes a plurality of photodetection cells arrayed two-dimensionally. Each of the photodetection cells accumulates the first component, which includes a reflected light pulse 19a attributed to the leading light pulse in each of the light pulse groups 8b, as the first signal charge 18a and accumulates the second component, which is included in the falling period 13 of the last reflected light pulse in a reflected light pulse group 19b attributed to each of the light pulse groups 8b, as the second signal charge 18b. Furthermore, each of the photodetection cells outputs, as the first electric signal 15a, an electric signal corresponding to a total amount of the first signal charge 18a accumulated within a first period serving as one frame period and outputs, as the second electric signal 15b, an electric signal corresponding to a total amount of the second signal charge 18b accumulated within the first period. This makes it possible to acquire biological information about the blood flow of the target part 6 as a moving image including a plurality of frames.

In the example shown in FIG. 4, a reflected light pulse from the target part that corresponds to the leading light pulse in one light pulse group within one frame is detected as the first component, and a reflected light pulse from the target part that corresponds to the falling period 13 of the last light pulse in the same light pulse group within the same frame is detected as the second component. In another example, a reflected light pulse from the target part that corresponds to the leading light pulse in each of some of a plurality of light pulse groups within one frame may be detected as the first component, and a reflected light pulse from the target part that corresponds to the falling period 13 of the last light pulse in each of the other light pulse groups within the same frame may be detected as the second component. For example, concerning reflected light pulses from the target part that correspond to a plurality of light pulse groups within one frame shown in the middle row of FIG. 4, only the first component may be detected from reflected light pulse groups corresponding to the odd-numbered light pulse groups, and only the second component may be detected from reflected light pulse groups corresponding to the even-numbered light pulse groups. Alternatively, only the second component may be detected from the reflected light pulse groups corresponding to the odd-numbered light pulse groups, and only the first component may be detected from the reflected light pulse groups corresponding to the even-numbered light pulse groups.

Next, the superimposition of the information on brain blood flow and the information on scalp blood flow onto the second electric signal 15b is described with reference to FIGS. 5A and 5B.

Figure 5A:
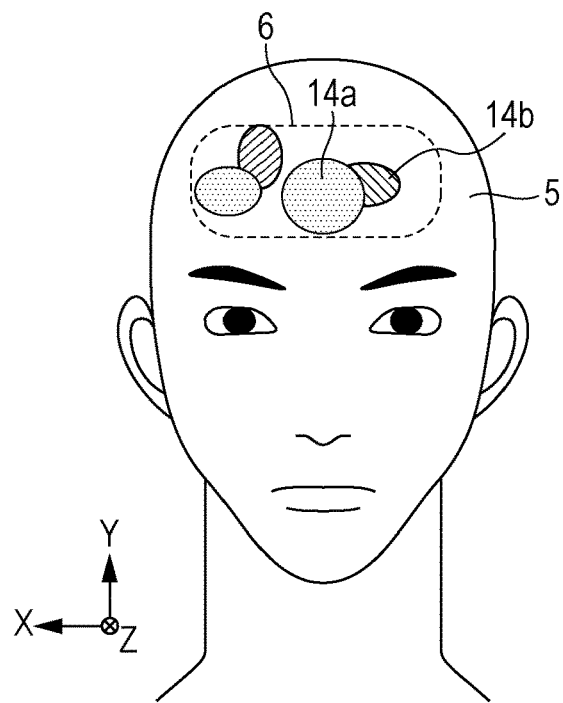
FIG. 5A is a front view showing changes in blood flow that are present in the surface and interior of a target part.
Figure 5B:
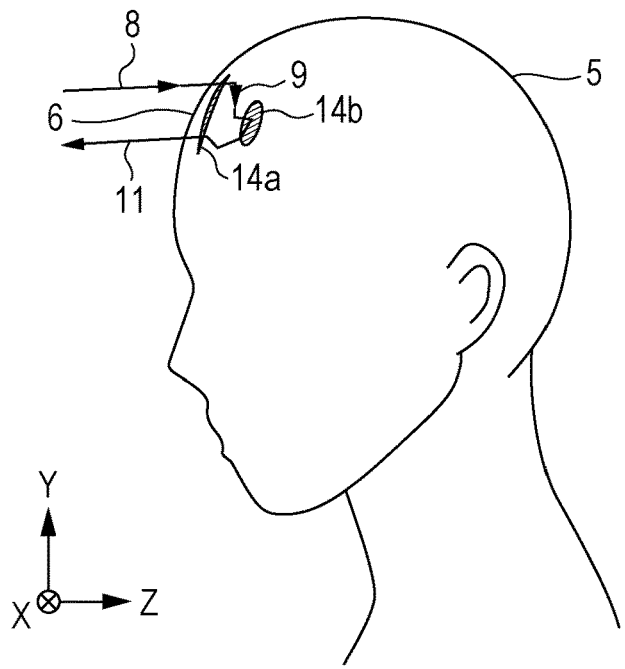
FIG. 5B is a cross-sectional view, taken along a Y-Z plane, showing the changes in blood flow that are present in the surface and interior of the target part.

FIG. 5A is a front view showing changes in blood flow that are present in the surface and interior of the target part 6. FIG. 5B is a cross-sectional view, taken along a Y-Z plane, showing the changes in blood flow that are present in the surface and interior of the target part 6. FIGS. 5A and 5B show a region 14a and a region 14b. The region 14a, located at a depth of, for example, approximately 3 to 6 mm in the epidermis from the surface of the target part 6, which is a forehead, is a region of scalp blood flow, which is blood flow near the surface. The region 14b is a region of brain blood flow, which is blood flow in the interior at a depth of approximately 10 to 18 mm from the surface. Attention is paid to the optical path through which the light 8 enters the target part 6 and is detected as the internally-scattered light 9b by the photodetector 2. The internally-scattered light 9b, albeit depending on a blood flow distribution, passes through the region 14a first and then is scattered or absorbed to pass through the region 14b. Furthermore, the internally-scattered light 9b is repeatedly scattered or absorbed to pass through the region 14a again and come out of the target part 6. That is, the information on scalp blood flow is superimposed on the information on brain blood flow included in the falling period 13 of the last reflected light pulse in a reflected light pulse group 19b returning from the target part 6 due to each of the light pulse groups 8b. This causes deterioration in S/N ratio of the information on brain blood flow. The information on brain blood flow is influenced by the region 14a being superimposed thereonto on an outward path. However, the influence is made smaller by scattering or absorption on the outward and return optical paths in the living body. Therefore, the information on brain blood flow is greatly influenced by the region 14a being superimposed thereonto on a return path.

Next, a method for acquiring a distribution that indicates changes in blood flow in the target part 6 is described.

First, the control circuit 7 causes the photodetector 2, which is an image sensor, to output the following first to fourth image signals. The first image signal represents a two-dimensional distribution of a total amount of the first signal charge 18a accumulated in the plurality of photodetection cells during the first period. The second image signal represents a two-dimensional distribution of a total amount of the second signal charge 18b accumulated in the plurality of photodetection cells during a second period that is identical to or different from the first period. The third image signal represents a two-dimensional distribution of a total amount of the first signal charge 18a accumulated in the plurality of photodetection cells during a third period preceding the first period. The fourth image signal represents a two-dimensional distribution of a total amount of the second signal charge 18b accumulated in the plurality of photodetection cells during a fourth period preceding the second period.

Next, the signal processing circuit 30 receives the first to fourth image signals from the photodetector 2. After that, the signal processing circuit 30 generates a first difference image corresponding to a difference between an image represented by the first image signal and an image represented by the third image signal and generates a second difference image corresponding to a difference between an image represented by the second image signal and an image represented by the fourth image signal.

The first difference image is equivalent to a distribution that indicates changes in scalp blood flow in the target part 6, and the second difference image is equivalent to a distribution that indicates changes in scalp blood flow and brain blood flow in the target part 6. It is assumed herein that the first difference image is an image that uses the third image signal as a reference value and displays an increase or decrease in the first image signal from the reference value. Similarly, it is assumed herein that the second difference image is an image that uses the fourth image signal as a reference value and displays an increase or decrease in the second image signal from the reference value. When the signal processing circuit 30 receives the third and fourth image signals only once and repeatedly receives the first and second image signals every one-frame cycle, a moving image of a distribution that indicates changes in blood flow in the target part 6 is obtained.

As shown in the example of FIG. 4, the first and second periods may be the frame period, and the third and fourth periods may be the same frame period. As will be mentioned later, the second period may be a frame period that is different from the first period, and the fourth period may be a frame period that is different from the third period. In an example, the second period may be a frame period following the first period, and the fourth period may be a frame period following the third period.

Next, a method for improving the S/N ratio of the information on brain blood flow is described.

Figure 6A:
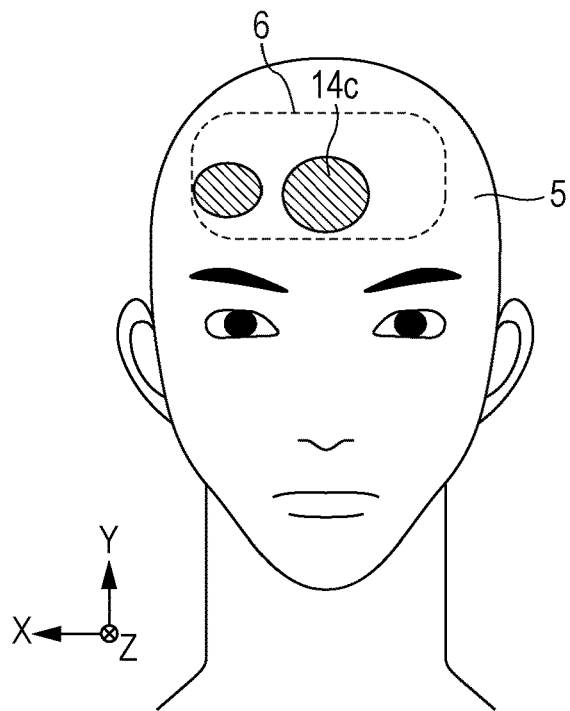
FIG. 6A is a diagram schematically showing changes in blood flow in the surface of the target part.
Figure 6B:
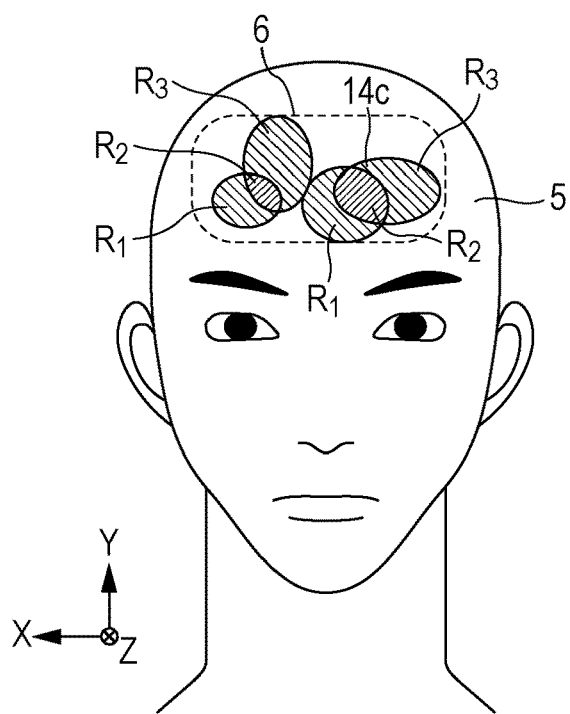
FIG. 6B is a diagram schematically showing changes in blood flow in the surface and interior of the target part.
Figure 6C:
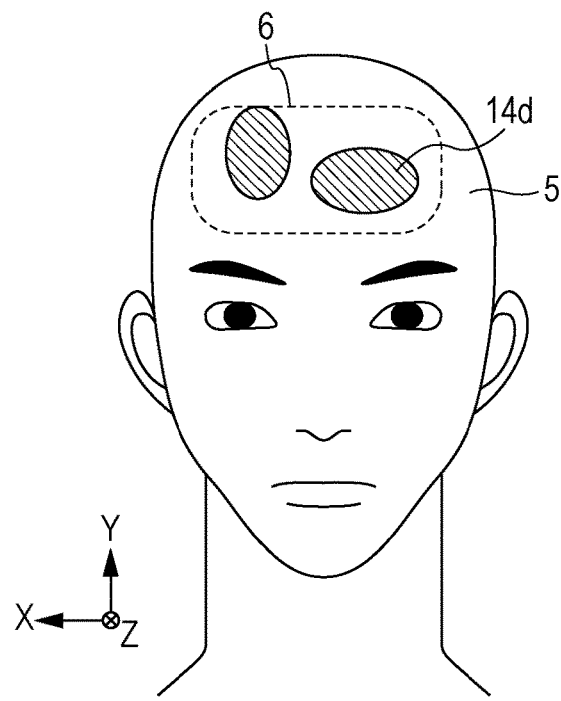
FIG. 6C is a diagram schematically showing changes in blood flow in the interior of the target part as derived by image computations.
Figure 6D:
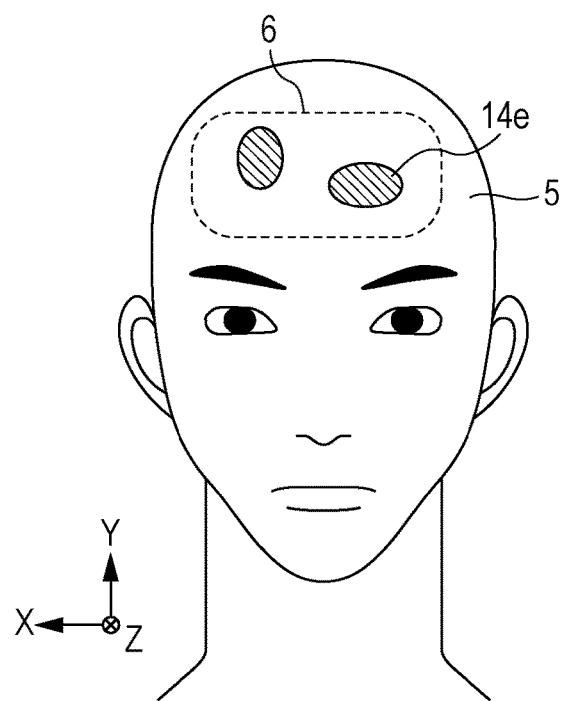
FIG. 6D is a diagram schematically showing changes in blood flow in the interior of the target part as image-corrected by further image computations.

FIG. 6A is a diagram schematically showing changes in blood flow in the surface of the target part 6. FIG. 6B is a diagram schematically showing changes in blood flow in the surface and interior of the target part 6. FIG. 6C is a diagram schematically showing changes in blood flow in the interior of the target part 6 as derived by image computations. FIG. 6D is a diagram schematically showing changes in blood flow in the interior of the target part 6 as image-corrected by further image computations.

In this example, as shown in FIG. 6A, the signal processing circuit 30 generates the first difference image, which represents a distribution of a region 14c in which there are temporal changes in scalp blood flow, in accordance with the first electric signal 15a, which represents the amount of the first signal charge 18a. Next, as shown in FIG. 6B, the signal processing circuit 30 generates the second difference image, which represents a distribution of the region 14c in which there are temporal changes in scalp blood flow or brain blood flow, in accordance with the second electric signal 15b, which represents the amount of the second signal charge 18b. The region 14c in FIG. 6B includes a region $R_1$ that includes the information on scalp blood flow and does not include the information on brain blood flow, a region $R_2$ that includes the information on both scalp blood flow and brain blood flow, and a region $R_3$ that includes the information on brain blood flow and does not include the information on scalp blood flow.

The signal processing circuit 30 generates blood flow information on the interior of the target part 6 through computations based on the first electric signal 15, which represents the amount of the first signal charge 18a, and the second electric signal 15b, which represents the amount of the second signal charge 18b. The first signal charge 18a includes blood flow information on the surface of the target part 6, and the second signal charge 18b includes blood flow information on the surface and interior of the target part 6.

Through image computations including subtractions and divisions based on the two two-dimensional images in FIGS. 6A and 6B, the signal processing circuit 30 generates a two-dimensional image corresponding to a distribution of a region 14d in FIG. 6C that indicates changes in brain blood flow. For example, the signal processing circuit 30 makes a correction so that the two signals become equal in intensity in the region $R_1$ in FIG. 6B and a region in FIG. 6A that is equivalent to the region $R_1$. After that, it is only necessary to subtract, from the distribution in FIG. 6B that indicates the blood flow information on the surface and the interior, the distribution in FIG. 6A that indicates the blood flow information on the surface. This gives a distribution, such as that shown, for example, in FIG. 6C, that indicates the blood flow information on the interior.

The two-dimensional image in FIG. 6C represents the distribution of the region 14d of change in brain blood flow. The region 14d of change in brain blood flow is in a spread state due to scattering of brain blood flow in the interior. To address this problem, the signal processing circuit 30 makes an image correction by guessing the scattering state through a diffusion equation or a Monte Carlo analysis. By so doing, the signal processing circuit 30 generates a two-dimensional image corresponding to a distribution of a region 14e of change in brain blood flow such as that shown in FIG. 6D. This two-dimensional image is a desired image that indicates changes in brain blood flow.

In this method, for computations at high S/N ratios, it is possible, for example, to equalize the luminances of regions in the two images in FIGS. 6A and 6B that indicate changes in blood flow in the surface of the target part 6.

A first region is a region 14c in the image of FIG. 6A that is formed by a plurality of pixels having pixel values exceeding a threshold. Similarly, a second region is a region 14c in the image of FIG. 6B that is formed by a plurality of pixels having pixel values exceeding the threshold. The threshold may be set to be such a small value as to exceed a noise level. $M_1$ is the average pixel value of a part of the first region in the image of FIG. 6A that overlaps the second region. Similarly, $M_2$ is the average pixel value of a part of the second region in the image of FIG. 6B that overlaps the first region. In this case, it may be, for example, that $M_1=M_2$. In actuality, since a correction of approximately one digit is possible with an image correction, the ratio between $M_1$ and $M_2$ may for example be kept in the order of one digit. That is, the average pixel value $M_1$, which is obtained by the first component, and the average pixel value $M_2$, which is obtained by the second component, may satisfy, for example, $0.1 \leq M_1/M_2 \leq 10$. Further, $0.03 \leq M_1/M_2 \leq 30$ may be satisfied. The condition can be attained by adjusting at least one of the pulse widths $T_1$ and $T_2$, the timing of opening and closing of the electronic shutter in the storage section 4a, and the timing of opening of the electronic shutter in the storage section 4b.

The part of the region 14c in the example of FIG. 6A that overlaps the second region 14c in the example of FIG. 6B includes the information on scalp blood flow and does not include the information on brain blood flow. Meanwhile, the part of the second region 14c in the example of FIG. 6B that overlaps the region 14c in the example of FIG. 6A includes part of the information on brain blood flow as well as the information on scalp blood flow. In this case, too, as mentioned above, the ratio of $M_1$ to $M_2$ has a difference of approximately one digit. Therefore, there is no problem even if $M_2$ includes part of the information on brain blood flow.

Next, some modifications of the biological measuring device 17 according to Embodiment 1 are described.

FIG. 7 is a diagram schematically showing a time distribution (upper row) of light pulse groups 8b, a time distribution (middle row) of a light power that is detected by the photodetector 2, and the timing and charge storage (lower row) of the electronic shutter according to a first modification of Embodiment 1.

In the example shown in FIG. 7, the first component, which includes a reflected light pulse 19a from the target part 6 that is attributed to the leading light pulse included in each of the light pulse groups 8b, is accumulated as the first signal charge 18a in the storage section 4a within one frame period. After the end of one frame period, the first signal charge 18a is outputted as the first electric signal 15a, which includes the information on scalp blood flow, to the control circuit 7. On the other hand, unlike in the example shown in FIG. 4, the second signal charge 18b is not accumulated. The first modification is effective in a case where there is no need for information on brain blood flow but there is need for information on scalp blood flow. Thus, the technology of the present disclosure is not necessarily limited to a use in which information on brain blood flow is acquired.

FIG. 8 is a diagram schematically showing a time distribution (upper row) of light pulse groups 8b and single light pulses 8A, a time distribution (middle row) of a light power that is detected by the photodetector 2, and the timing and charge storage (lower row) of the electronic shutter according to a second modification of Embodiment 1. The following omits a description that overlaps the already-described contents.

As shown in the upper row of FIG. 8, the light source 1 emits light pulse groups 8b and single light pulses 8A in sequence. Each of the light pulse groups 8b has a pulse width $T_1$ and a maximum light power value $P_2$, and each of the single light pulses 8A has a pulse width $T_3$ and a maximum light power value $P_1$. Each of the light pulse groups 8b includes three light pulses.

As indicated in the middle row of FIG. 8, reflected light pulses 19A returning from the target part 6 due to the single light pulses 8A each have a pulse width $T_{d3}$, which is substantially the same as $T_3$. The reflected light pulses 19A have shapes that become slightly wider toward the skirts due to the occurrence of time delays under the influence of internal scattering.

The photodetector 2 photoelectrically converts, through the photoelectric conversion element 3, a component of light including all of the reflected light pulses groups 19b returning from the target part 6 due to the light pulse groups 8b and a component of light included in the falling periods 13 of the reflected light pulses 19A returning from the target part 6 due to the signal light pulses 8A and accumulates the first signal charge 18a and the second signal charge 18b in the storage sections 4a and 4b, respectively.

In the first modification, the pulse width $T_2$ of each of the light pulse groups 8b is shorter than the pulse width $T_3$ of each of the single light pulses 8A ($T_2<T_3$). For example, $T_2=1$ to 3 ns and $T_3=11$ to 22 ns. The maximum light power value $P_2$ of each of the light pulse groups 8b is lower than the maximum light power value $P_1$ of each of the single light pulses 8A ($P_2<P_1$). For example, $P_2/P_1=0.01$ to 0.1. By adjusting at least one of $P_1$, $P_2$, $T_{S1}$, and $T_{S2}$, the amounts of storage of the first signal charge 18a and the second signal charge 18b can be kept substantially the same or the signal charge ratio can be kept in the order of one digit.

As in the first modification, the control circuit 7 may cause the light source 1 to emit one or more single light pulses 8A at a timing that is different from a timing at which one or more light pulse groups 8b are emitted. In this case, the control circuit 7 causes the photodetector 2 to detect a second component within the first period. The second component is a component of light included in the falling period 13 of each of one or more single reflected light pulses 19A reflected by the target part 6. After that, the control circuit 7 causes the photodetector 2 to output a second electric signal corresponding to the second component.

Even with such a configuration, as with the example shown in FIG. 4, it is possible to detect blood flow information on the surface of the target part that is included in a front-end part of a light pulse group and detect blood flow information on the interior of the target part that is included in a rear-end part of a single light pulse.

Furthermore, a component of light including a part of a reflected light pulse group 19b returning from the target part 6 due to a light pulse group 8b may be detected by adjusting the timing of the electronic shutter. For example, any one of a component including only a reflected light pulse in a leading region of a reflected light pulse group 19b, a component including only a reflected light pulse in the leading region to a central region of the reflected light pulse group 19b, a component including only a reflected light pulse in the central region of the reflected light pulse group 19b, and a component including only a reflected light pulse in the central region to a rear region of the reflected light pulse group 19b may be detected.

Embodiment 2

Next, a biological measuring device according to Embodiment 2 of the present disclosure is described with reference to FIGS. 9A and 9B with a focus on differences from the biological measuring device 17 according to Embodiment 1.

Figure 9B:
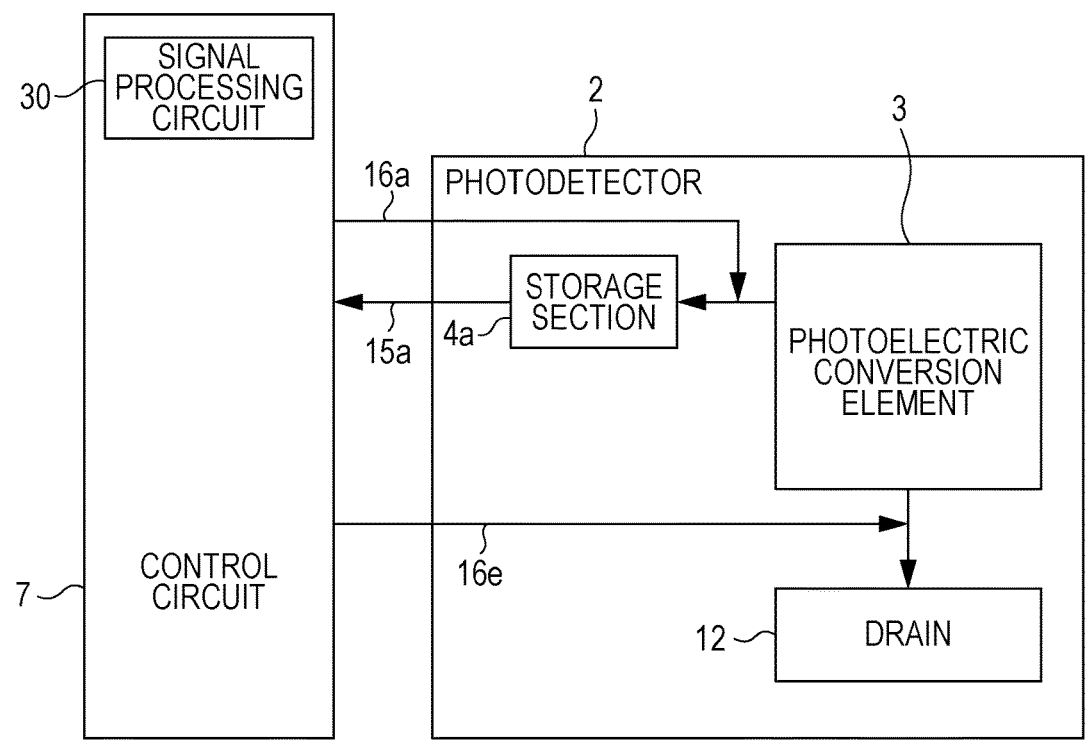
FIG. 9B is a diagram schematically showing an internal configuration of the photodetector according to Embodiment 2 and the flow of electric signals and control signals.

FIG. 9A is a diagram schematically showing a time distribution (upper row) of light pulse groups 8b, a time distribution (middle row) of a light power that is detected by the photodetector 2, and the timing and charge storage (lower row) of an electronic shutter according to Embodiment 2 of the present disclosure. FIG. 9B is a diagram schematically showing an internal configuration of the photodetector 2 according to Embodiment 2 and the flow of electric signals and control signals.

In Embodiment 2, the control circuit 7 causes the light source 1 to emit at least one light pulse group 8b within a first frame period. The control circuit 7 causes the photodetector 2 to detect a first component that is a component of light including the leading reflected light pulse 19a in a reflected light pulse group 19b returning from the target part 6 and output a first electric signal corresponding to the first component. Furthermore, within a second frame period that follows the first frame period, the control circuit 7 causes the photodetector 2 to detects a second component within a second frame period that follows the first frame period. The second component is a component of light included in the falling period 13 of the last reflected light pulse in a reflected light pulse group 19d returning from the target part 6. After that, the control circuit 7 causes the photodetector 2 to output a second electric signal corresponding to the second component.

The biological measuring device according to Embodiment 2 differs from the biological measuring device 17 according to Embodiment 1 in that each of the photodetection cells of the photodetector 2 includes only one storage section 4a and the first and second components are detected in different frame periods.

In the case of execution of the aforementioned method for acquiring a distribution that indicates changes in blood flow in the target part 6 in Embodiment 2, the first period is equivalent to the first frame period, the second period is equivalent to the second frame period, and the fourth period is equivalent to a frame period that follows the third period. As mentioned above, information on the distribution that indicates changes in scalp blood flow in the target part 6 and information on the distribution that indicates changes in scalp blood flow and brain blood flow in the target part 6 can be obtained from the first to fourth electric signals. A moving image may be generated by repeating this operation. Contrary to the example shown in FIG. 9A, the second component may be detected in the first frame period, and the first component may be detected in the second frame period.

In Embodiment 2, since each of the photodetection cells of the photodetector 2 includes only one storage section 4a, it is unnecessary to switch the storage section 4a. This brings about an effect of making the configuration simple and making control easy. The operation according to Embodiment 2 is also applicable to a configuration in which the photodetector 2 includes a plurality of storage sections. In that case, it is only necessary to use one of the plurality of storage sections.

In Embodiment 2, the method for acquiring information on the rear-end part of a pulse in the second frame period may be replaced by the method for acquiring information on the rear-end part of a pulse shown in FIG. 8. In that case, in the second frame period, the control circuit 7 causes the light source 1 to emit not a light pulse group but one or more light pulses and causes the photodetector 2 to detect a second component that is a component of light included in a falling period of each reflected light pulse. The control circuit 7 causes the photodetector 2 to output a second electric signal corresponding to the second component.

With such an operation, as with the example shown in FIG. 9A, it is possible to acquire blood flow information on the surface of the target part and blood flow information on the interior of the target part.

Embodiment 3

Next, a biological measuring device 17 according to Embodiment 3 of the present disclosure is described with reference to FIGS. 10A, 10B, and 11 with a focus on differences from the biological measuring device 17 according to Embodiment 1.

Figure 10A:
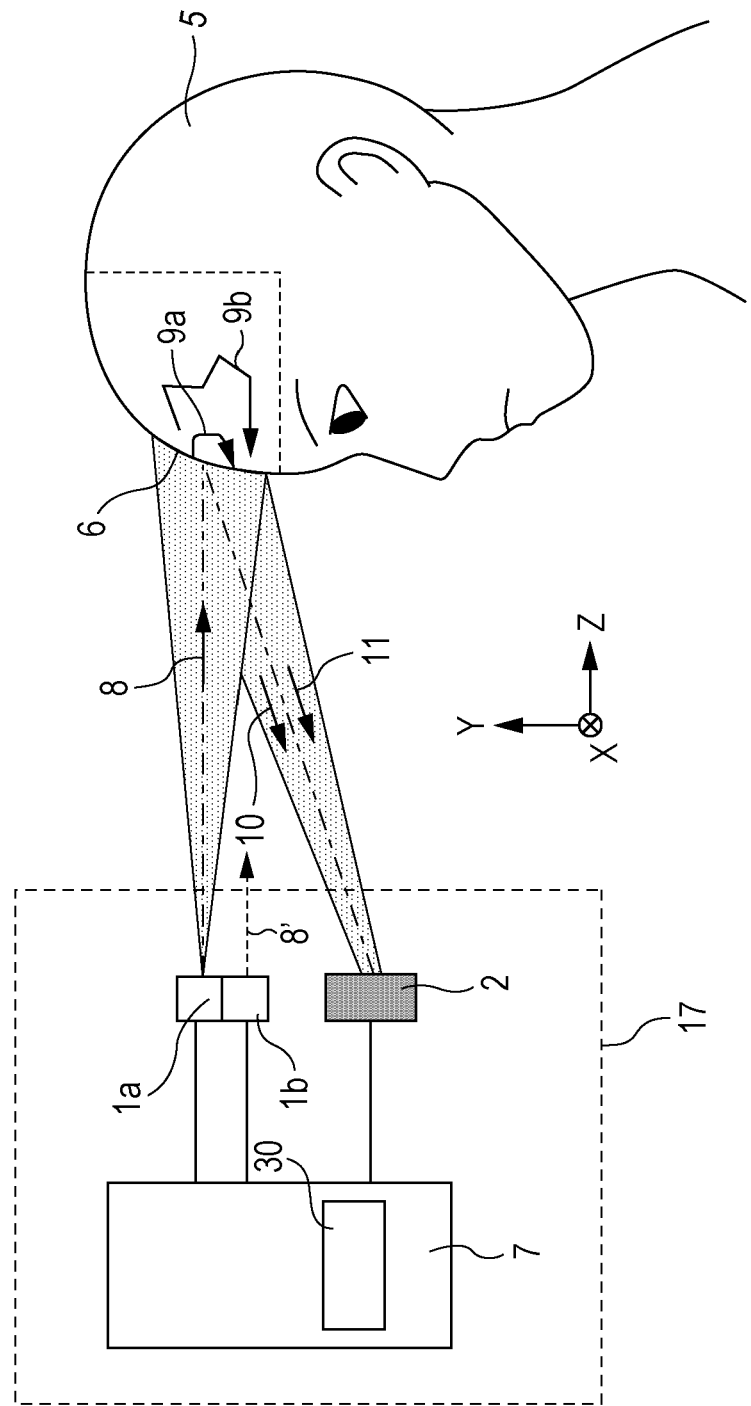
FIG. 10A is a schematic view for explaining a configuration of a biological measuring device according to Embodiment 3 and the way in which a biological measurement is carried out.
Figure 10B:
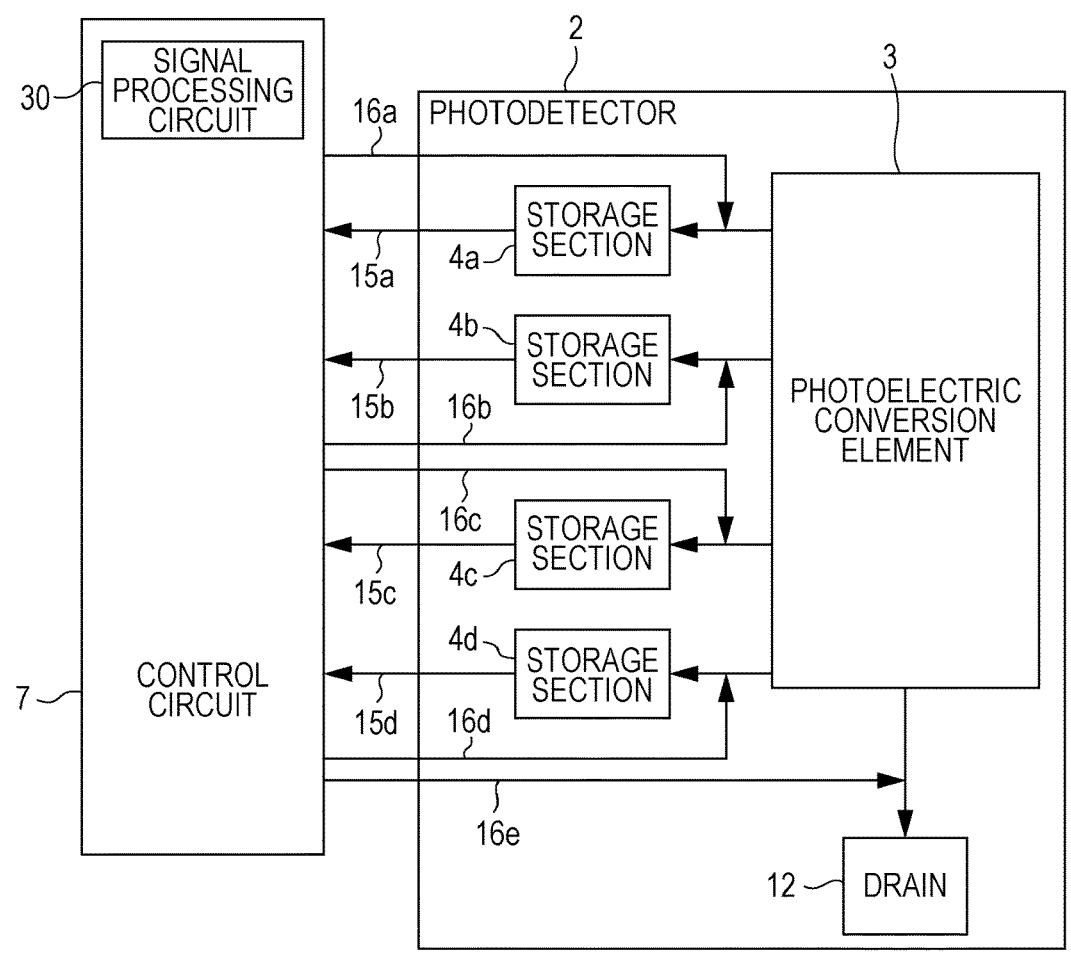
FIG. 10B is a diagram schematically showing an internal configuration of a photodetector according to Embodiment 3 and the flow of electric signals and control signals.

FIG. 10A is a schematic view for explaining a configuration of a biological measuring device 17 according to Embodiment 3 and the way in which a biological measurement is carried out. FIG. 10B is a diagram schematically showing an internal configuration of a photodetector 2 according to Embodiment 3 and the flow of electric signals and control signals.

FIG. 11 is a diagram schematically showing a time distribution (upper row) of light pulse groups 8b and 8d, a time distribution (middle row) of a light power that is detected by the photodetector 2, and the timing and charge storage (lower row) of an electronic shutter according to Embodiment 3.

The biological measuring device 17 according to Embodiment 3 differs from the biological measuring device 17 according to Embodiment 1 in that the light source 1 is a multiwavelength light source that emits light pulse groups 8b and 8d of different wavelengths in sequence.

The light source 1 is composed of a plurality of light-emitting elements 1a and 1b arranged side by side in a Y direction. The light-emitting element 1a emits light of a first wavelength range, and the light-emitting element 1b emits light of a second wavelength range that is different from the first wavelength range. The light-emitting elements 1a and 1b are for example laser chips.

The absorptance of oxyhemoglobin and deoxyhemoglobin varies, for example, at wavelengths of $\lambda_1=750$ nm and $\lambda_2=850$ nm. Therefore, computing two electric signals respectively obtained by using these two wavelengths makes it possible to measure the proportions of oxyhemoglobin and deoxyhemoglobin in the target part 6.

When the target part 6 is a forehead area of the head of a living body, the amount of change in brain blood flow in the frontal lobe, the amounts of change in oxyhemoglobin concentration and deoxyhemoglobin concentration, or the like can be measured. This makes sensing of information such as emotions possible. For example, in a centered state, there occur an increase in brain blood flow volume, an increase in amount of oxyhemoglobin, and the like.

Various combinations of wavelengths are possible. At a wavelength of 805 nm, the rates of absorption of oxyhemoglobin and deoxyhemoglobin become equal. Therefore, in view of the biological window, for example, a combination of a wavelength of not shorter than 650 nm and shorter than 805 nm and a wavelength of longer than 805 nm and not longer than 950 nm may be used. In this case, the control circuit 7 causes the light source 1 to emit light pulse groups 8b and 8d by alternately repeatedly emitting a light pulse group 8b of a wavelength of not shorter than 650 nm to shorter than 805 nm and a light pulse group 8d of a wavelength of longer than 805 nm to not longer than 950 nm.

A wavelength of 805 nm may be used in addition to the two wavelengths. In a case where three wavelengths of light are used, three laser chips are needed; however, since information on the third wavelength is obtained, utilizing the information may make computations easy.

The photodetector 2 of the biological measuring device 17 according to Embodiment 3 includes an electronic shutter that switches between storing signal charge and not storing signal charge and four storage sections 4a, 4b, 4c, and 4d. The light-emitting element 1a emits a light pulse group 8b of a wavelength $\lambda_1$. The photoelectric conversion element 3 photoelectrically converts a first component including a reflected light pulse 19a returning from the target part 6 due to the leading light pulse 8a. After that, in reaction to control signals 16a, 16b, 16c, 16d, and 16e from the control circuit 7, the photodetector 2 selects the storage section 4a and accumulates the first signal charge 18a for a period of time $T_{S1}$ of, for example, 11 to 22 ns. After the period of time $T_{S1}$ has elapsed, in reaction to the control signals 16a, 16b, 16c, 16d, and 16e from the control circuit 7, the photodetector 2 selects the drain 12 and releases an electric charge from the photoelectric conversion element 3.

Similarly, the photoelectric conversion element 3 photoelectrically converts a second component included in the falling period 13 of the last reflected light pulse in a reflected light pulse group 19b retuning from the target part 6 due to a light pulse group 8b of the wavelength $\lambda_1$. After that, in reaction to the control signals 16a, 16b, 16c, 16d, and 16e from the control circuit 7, the photodetector 2 selects another storage section 4b and accumulates the second signal charge 18b for a period of time $T_{S2}$ of, for example, 11 to 22 ns. After the period of time $T_{S2}$ has elapsed, in reaction to the control signals 16a, 16b, 16c, 16d, and 16e from the control circuit 7, the photodetector 2 selects the drain 12 and releases an electric charge from the photoelectric conversion element 3.

After this, the biological measuring device 17, replacing the light-emitting element 1a with the light-emitting element 1b, similarly emits a light pulse group 8d of a wavelength $\lambda_2$. The storage section 4c detects a component of light corresponding to the leading reflected light pulse 19c, and the storage section 4d detects a component of light corresponding to the falling period 13 of the last reflected light pulse in the reflected light pulse 19d.

Thus, the first component, which includes the leading reflected light pulse 19a in each reflected light pulse group 19b of the wavelength $\lambda_1$, is accumulated as the first signal charge 18a in the storage section 4a during one frame period. After the end of this frame period, the first signal charge 18a is outputted as a first electric signal 15a to the control circuit 7. The first electric signal 15a mainly includes the information on scalp blood flow of the wavelength $\lambda_1$.

The second component, which is included in the falling period 13 of the last reflected light pulse in each reflected light pulse group 19b of the wavelength $\lambda_1$, is accumulated as the second signal charge 18b in the storage section 4b during the same frame period. After the end of this frame period, the second signal charge 18b is outputted as a second electric signal 15b to the control circuit 7. The second electric signal 15b includes the information on scalp blood flow of the wavelength $\lambda_1$ as well as the information on brain blood flow of the wavelength $\lambda_1$.

A third light component including the leading reflected light pulse 19c in each reflected light pulse group 19d of the wavelength $\lambda_2$ is accumulated as a third signal charge 18c in the storage section 4c during the same frame period. After the end of this frame period, the third signal charge 18c is outputted as a third electric signal 15c to the control circuit 7. The third electric signal 15c mainly includes the information on scalp blood flow of the wavelength $\lambda_2$.

A fourth light component included in the falling period 13 of the last reflected light pulse in each reflected light pulse group 19d of the wavelength $\lambda_2$ is accumulated as a fourth signal charge 18d in the storage section 4d during the same frame period. After the end of this frame period, the fourth signal charge 18d is outputted as a fourth electric signal 15d to the control circuit 7. The fourth electric signal 15d includes the information on scalp blood flow of the wavelength $\lambda_2$ as well as the information on brain blood flow of the wavelength $\lambda_2$.

On the basis of the first to fourth electric signals, the signal processing circuit 30 generates four pieces of image information, respectively. Then, from these four pieces of image information, the signal processing circuit 30 generates, for example, an image of two two-dimensional concentration distributions of oxyhemoglobin and deoxyhemoglobin as an image that indicates changes in brain blood flow.

In another example, a reflected light pulse from the target part that corresponds to the leading light pulse in each of some of a plurality of light pulse groups of the wavelength $\lambda_1$ within one frame may be detected as the first component, and a reflected light pulse from the target part that corresponds to the falling period 13 of the last light pulse in each of the other light pulse groups within the same frame may be detected as the second component. Similarly, a reflected light pulse from the target part that corresponds to the leading light pulse in each of some of a plurality of light pulse groups of the wavelength $\lambda_2$ within one frame may be detected as the third component, and a reflected light pulse from the target part that corresponds to the falling period 13 of the last light pulse in each of the other light pulse groups within the same frame may be detected as the fourth component.

Next, a biological measuring device according to a modification of Embodiment 3 of the present disclosure is described.

Figure 12:
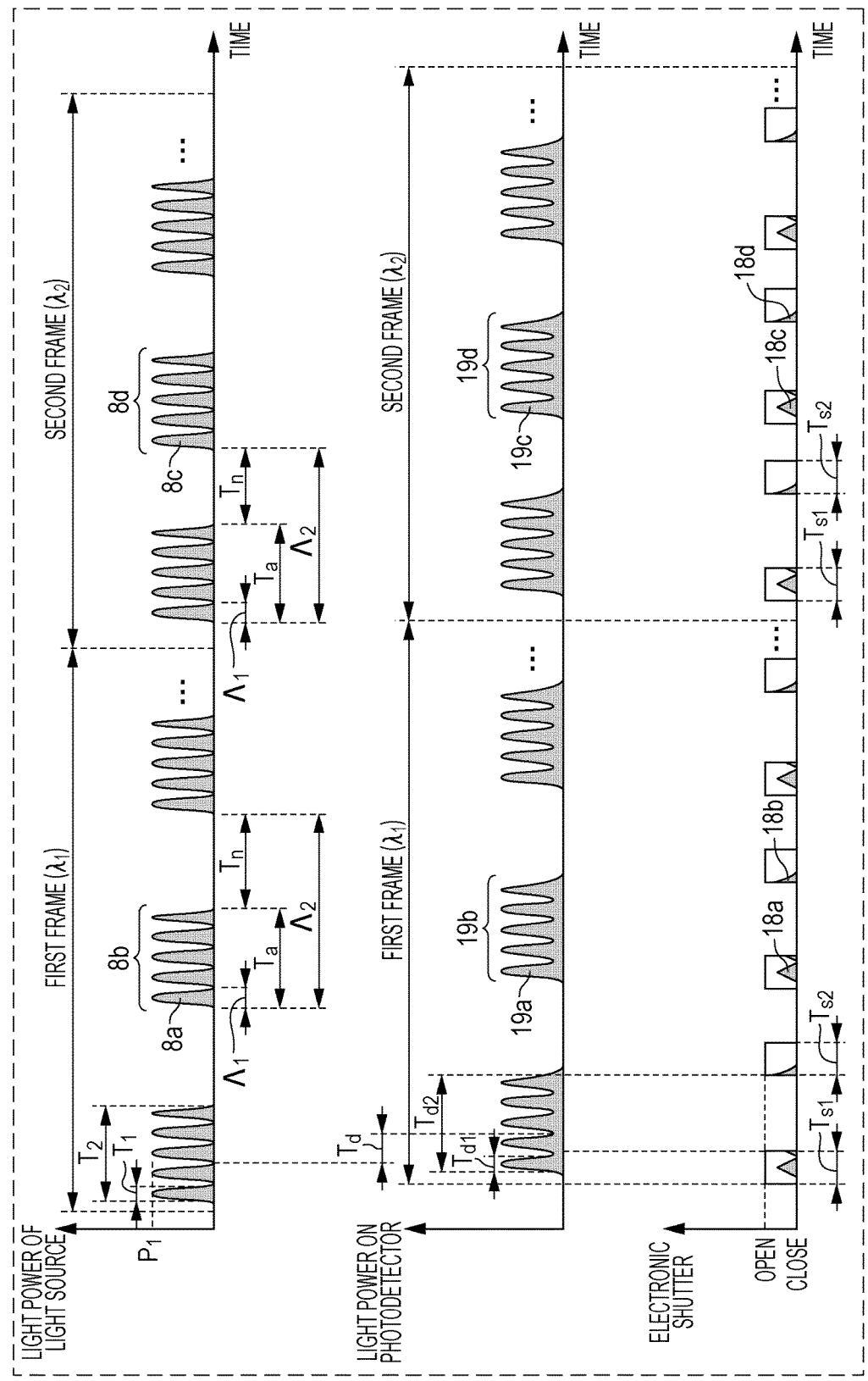
FIG. 12 is a diagram schematically showing a time distribution (upper row) of light pulse groups, a time distribution (middle row) of a light power that is detected by the photodetector, and the timing and charge storage (lower row) of the electronic shutter according to a first modification of Embodiment 3.

FIG. 12 is a diagram schematically showing a time distribution (upper row) of light pulse groups 8b and 8d, a time distribution (middle row) of a light power that is detected by the photodetector 2, and the timing and charge storage (lower row) of the electronic shutter according to a first modification of Embodiment 3 of the present disclosure.

In this example, the acquisition of blood flow information by light of the wavelength $\lambda_1$ and the acquisition of blood flow information by light of the wavelength $\lambda_2$ are performed in different frame periods. In this example, two storage sections 4a and 4b are used.

During a first frame period, a light pulse group 8b having a first wavelength $\lambda_1$ is repeatedly emitted. An electric charge of a first component that is equivalent to the front-end part of each reflected light pulse group 19b is accumulated in one storage section 4a. An electric charge of a second component that is equivalent to the rear-end part of each reflected light pulse group 19b is accumulated in the other storage section 4b. After the end of the first frame period, the control circuit 7 reads out a first electric signal and a second electric signal from these two storage sections 4a and 4b, respectively.

During a second frame period, a light pulse group 8d having a second wavelength $\lambda_2$ is repeatedly emitted. An electric charge of a third component that is equivalent to the front-end part of each reflected light pulse group 19d is accumulated in one storage section 4a. An electric charge of a fourth component that is equivalent to the rear-end part of each reflected light pulse group 19d is accumulated in the other storage section 4b. After the end of the second frame period, the control circuit 7 reads out a third electric signal and a fourth electric signal from these two storage sections 4a and 4b, respectively.

In another example, a reflected light pulse from the target part that corresponds to the leading light pulse in each of some of a plurality of light pulse groups within a first frame may be detected as the first component, and a reflected light pulse from the target part that corresponds to the falling period 13 of the last light pulse in each of the other light pulse groups may be detected as the second component. Similarly, a reflected light pulse from the target part that corresponds to the leading light pulse in each of some of a plurality of light pulse groups within a second frame may be detected as the third component, and a reflected light pulse from the target part that corresponds to the falling period 13 of the last light pulse in each of the other light pulse groups may be detected as the fourth component.

Figure 13:
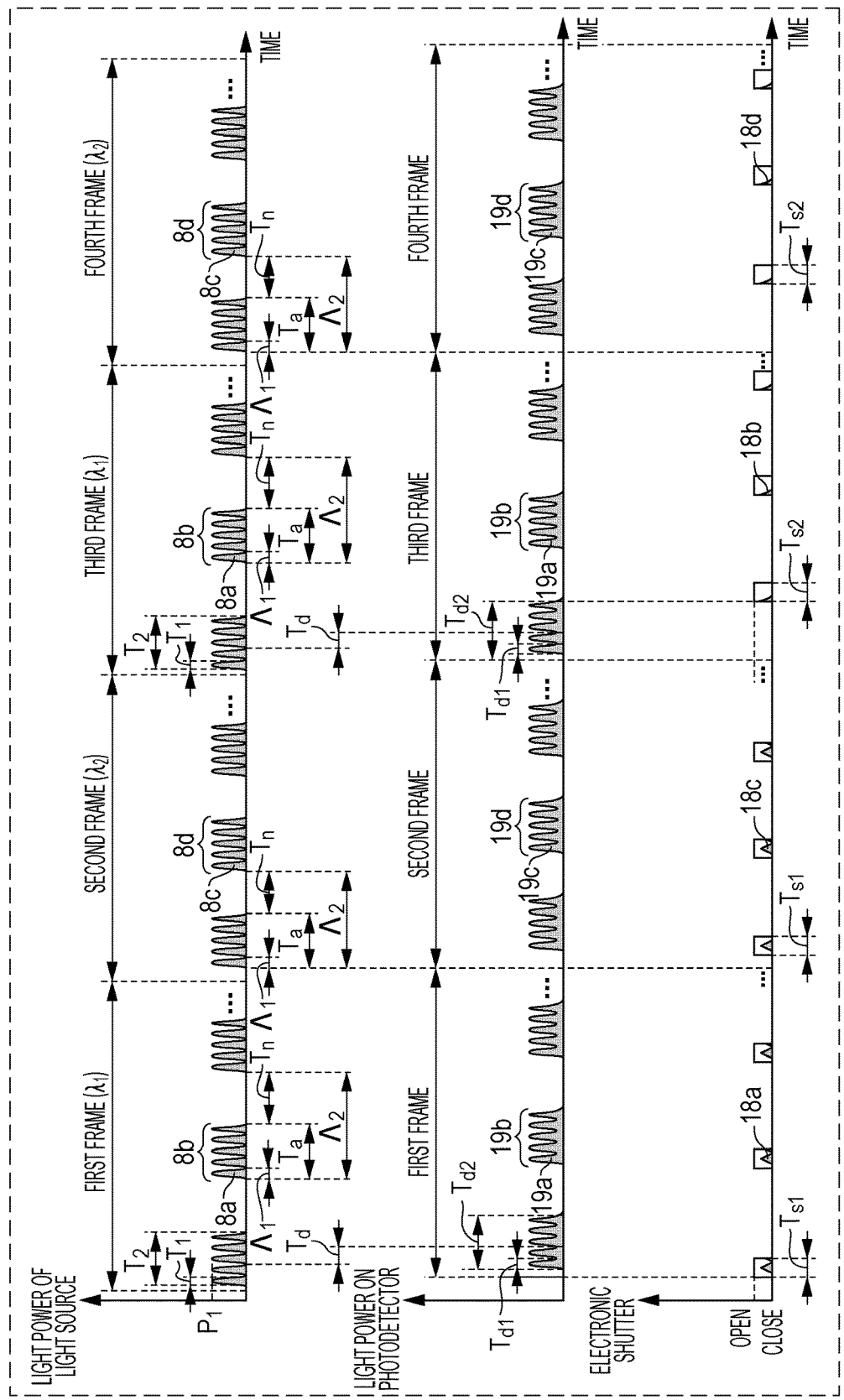
FIG. 13 is a diagram schematically showing a time distribution (upper row) of light pulse groups, a time distribution (middle row) of a light power that is detected by the photodetector, and the timing and charge storage (lower row) of the electronic shutter according to a second modification of Embodiment 3.

FIG. 13 is a diagram schematically showing a time distribution (upper row) of light pulse groups 8b and 8d, a time distribution (middle row) of a light power that is detected by the photodetector 2, and the timing and charge storage (lower row) of the electronic shutter according to a second modification of Embodiment 3 of the present disclosure. In this example, the acquisition of blood flow information on the surface of the target part by light of the wavelength $\lambda_1$, the acquisition of blood flow information on the surface of the target part by light of the wavelength $\lambda_2$, the acquisition of blood flow information on the interior of the target part by light of the wavelength $\lambda_1$, and the acquisition of blood flow information on the interior of the target part by light of the wavelength $\lambda_2$ are all performed in different frame periods. In this example, each of the photo-detection cells of the photodetector 2 needs only include one storage section.

During a first frame period, a light pulse group 8b having a first wavelength $\lambda_1$ is repeatedly emitted. An electric charge of a first component that is equivalent to the front-end part of each reflected light pulse group 19b is accumulated in the storage section. After the end of the first frame period, the control circuit 7 reads out a first electric signal from the storage section.

During a second frame period, a light pulse group 8d having a second wavelength $\lambda_2$ is repeatedly emitted. An electric charge of a third component that is equivalent to the front-end part of each reflected light pulse group 19d is accumulated in the storage section. After the end of the second frame period, the control circuit 7 reads out a third electric signal from the storage section.

During a third frame period, a light pulse group 8b having the first wavelength $\lambda_1$ is repeatedly emitted. An electric charge of a second component that is equivalent to the rear-end part of each reflected light pulse group 19b is accumulated in the storage section. After the end of the third frame period, the control circuit 7 reads out a second electric signal from the storage section.

During a fourth frame period, a light pulse group 8d having the second wavelength $\lambda_2$ is repeatedly emitted. An electric charge of a fourth component that is equivalent to the rear-end part of each reflected light pulse group 19d is accumulated in the storage section. After the end of the fourth frame period, the control circuit 7 reads out a fourth electric signal from the storage section.

According to the foregoing operation, each of the photo-detection cells of the photodetector 2 needs only include one storage section. This eliminates the need to switch between storage sections, thus making it possible to achieve a simple configuration.

In the foregoing, the biological measuring devices according to Embodiments 1 to 3 have been described. However, the present disclosure is not limited to these embodiments. A biological measuring device based on a combination of the configurations of the biological measuring devices according to the respective embodiments is also encompassed in the present disclosure and can bring about similar effects.

What is claimed is:

1. A measuring device comprising:
   a light source that emits at least one light pulse group toward a target part of an object, the at least one light pulse group each including light pulses emitted sequentially;
   a photodetector that detects at least a part of at least one reflected light pulse group, the at least one reflected light pulse group including reflected light pulses sequentially returning from the target part; and
   a control circuit that controls the light source and the photodetector, wherein:
   the control circuit causes the light source to emit the at least one light pulse group within a first period,
   the control circuit causes the photodetector to extract a first component within the first period, the first component being a component of light included in at least a part of a leading reflected light pulse of the reflected light pulses, and
   the control circuit causes the photodetector to output a first electric signal corresponding to the first component.

2. The measuring device according to claim 1, wherein:
   the control circuit further causes the photodetector to extract a second component within the first period, the second component being a component of light included in a last reflected light pulse of the reflected light pulses during a falling period, the falling period being a period from a point in time at which the last reflected light pulse starts decreasing in light power to a point in time at which the last reflected light pulse finishes decreasing in light power, and the control circuit causes the photodetector to output a second electric signal corresponding to the second component.

3. The measuring device according to claim 2, further comprising a signal processing circuit that generates blood flow information on the target part through a computation based on the first electric signal and the second electric signal.

4. The measuring device according to claim 3, wherein:
the first electric signal includes blood flow information on a surface of the target part,
the second electric signal includes the blood flow information on the surface of the target part and blood flow information on an interior of the target part, and
the signal processing circuit generates the blood flow information on the interior of the target part.

5. The measuring device according to claim 3, wherein:
the photodetector is an image sensor including photodetection cells arrayed two-dimensionally, and
each of the photodetection cells
accumulates the first component as a first signal charge,
accumulates the second component as a second signal charge,
outputs, as the first electric signal, an electric signal corresponding to a total amount of the first signal charge, and
outputs, as the second electric signal, an electric signal corresponding to a total amount of the second signal charge.

6. The measuring device according to claim 5, wherein:
the control circuit causes the image sensor to output
a first image signal corresponding to a first two-dimensional distribution of the total amount of the first signal charge accumulated in the photodetection cells during a first period,
a second image signal corresponding to a second two-dimensional distribution of the total amount of the second signal charge accumulated in the photodetection cells during a second period that is identical to or different from the first period,
a third image signal corresponding to a third two-dimensional distribution of the total amount of the first signal charge accumulated in the photodetection cells during a third period preceding the first period, and
a fourth image signal corresponding to a fourth two-dimensional distribution of the total amount of the second signal charge accumulated in the photodetection cells during a fourth period preceding the second period, and
the signal processing circuit
receives the first to fourth image signals from the image sensor,
generates a first difference image corresponding to a difference between the first image signal and the third image signal, and
generates a second difference image corresponding to a difference between the second image signal and the fourth image signal.

7. The measuring device according to claim 6, wherein $0.1 \leq M_1/M_2 \leq 10$ is satisfied when
the first difference image includes first pixels each of which has a pixel value exceeding a first threshold, the first pixels forming a first region,
the second difference image includes second pixels each of which has a pixel value exceeding a second threshold, the second pixels forming a second region,
$M_1$ is an average pixel value in a part of the first region that overlaps the second region, and
$M_2$ is an average pixel value in a part of the second region that overlaps the first region.

8. The measuring device according to claim 1, wherein:
the control circuit further causes the photodetector to extract a second component within a second period that is different from the first period, the second component being a component of light included in a last reflected light pulse of the reflected light pulses during a falling period, the falling period being a period from a point in time at which the last reflected light pulse starts decreasing in light power to a point in time at which the last reflected light pulse finishes decreasing in light power, and
the control circuit causes the photodetector to output a second electric signal corresponding to the second component.

9. The measuring device according to claim 1, wherein:
the at least one light pulse group includes a first light pulse group and a second light pulse group,
the at least one reflected light pulse group includes a first reflected light pulse group and a second reflected light pulse group,
the first reflected light pulse group includes first reflected light pulses,
the second reflected light pulse group includes second reflected light pulses,
the control circuit causes the light source to emit the first light pulse group and the second light pulse group within the first period,
the second light pulse group is emitted at a timing that is different from a timing at which the first light pulse group is emitted,
the first component is a component of light included in at least a part of a leading first reflected light pulse of the first reflected light pulses,
the control circuit further causes the photodetector to extract a second component within the first period, the second component being a component of light included in a last second reflected light pulse of the second reflected light pulses during a falling period, the falling period being a period from a point in time at which the last second reflected light pulse starts decreasing in light power to a point in time at which the last second reflected light pulse finishes decreasing in light power, and
the control circuit causes the photodetector to output a second electric signal corresponding to the second component.

10. The measuring device according to claim 1, wherein:
the at least one light pulse group includes a first light pulse group and a second light pulse group,
the at least one reflected light pulse group includes a first reflected light pulse group and a second reflected light pulse group,
the first reflected light pulse group includes first reflected light pulses, the second reflected light pulse group includes second reflected light pulses, the control circuit causes the light source to emit the first light pulse group within the first period, the first component is a component of light included in at least a part of a leading first reflected light pulse of the first reflected light pulses, the control circuit further causes the light source to emit the second light pulse group within a second period that is different from the first period, the control circuit causes the photodetector to extract a second component within the second period, the second component being a component of light included in a last second reflected light pulse of the second reflected light pulses during a falling period, the falling period being a period from a point in time at which the last second reflected light pulse starts decreasing in light power to a point in time at which the last second reflected light pulse finishes decreasing in light power, and the control circuit causes the photodetector to output a second electric signal corresponding to the second component.

11. The measuring device according to claim 1, wherein:

the at least one light pulse group includes a first light pulse group including light pulses having a wavelength of not shorter than 650 nm to shorter than 805 nm and a second light pulse group including light pulses having a wavelength of longer than 805 nm to not longer than 950 nm, and the control circuit causes the light source to alternately emit the first light pulse group and the second light pulse group.

12. The measuring device according to claim 1, wherein each of the light pulses has a length of time of not shorter than 0.5 nanosecond to shorter than 3.0 nanoseconds.

13. The measuring device according to claim 1, wherein each of the light pulses has a length of time of not shorter than 0.5 nanosecond to shorter than 5.0 nanoseconds.

14. The measuring device according to claim 1, wherein:

the light source is a semiconductor laser, and by supplying the light source with a driving current on which a high-frequency component has been superimposed, the control circuit causes the light source to emit the at least one light pulse group.

15. The measuring device according to claim 1, wherein the light source is a self-oscillation laser.

16. A measuring device comprising:

a light source that emits at least one light pulse group and at least one second light pulse toward a target part of an object, the at least one light pulse group each including first light pulses emitted sequentially;

a photodetector that detects at least a part of at least one reflected light pulse group and at least a part of at least one second reflected light pulse returning from the target part, the at least one reflected light pulse group including first reflected light pulses sequentially returning from the target part; and a control circuit that controls the light source and the photodetector, wherein:

the control circuit causes the light source to emit the at least one light pulse group within a first period, the control circuit causes the photodetector to extract a first component within the first period, the first component being a component of light included in at least the part of the at least one reflected light pulse group, the control circuit causes the photodetector to output a first electric signal corresponding to the first component, the control circuit causes the light source to emit the at least one second light pulse at a timing within the first period or within a second period that is different from the first period, the timing being different from a timing at which the at least one light pulse group is emitted, the control circuit causes the photodetector to extract a second component within the first period or within the second period, the second component being a component of light included in the at least one second reflected light pulse during a falling period, the falling period being a period from a point in time at which the at least one second reflected light pulse starts decreasing in light power to a point in time at which the at least one second reflected light pulse finishes decreasing in light power, and the control circuit causes the photodetector to output a second electric signal corresponding to the second component.

17. The measuring device according to claim 16, wherein a light power of the at least one second light pulse is greater than a light power of each of the first light pulses.

* * * * *